US012576168B2

(12) United States Patent
Lu et al.

(10) Patent No.: US 12,576,168 B2
(45) **Date of Patent: *Mar. 17, 2026**

(54) PEPTIDE PET/SPECT PROBES SPECIFIC TO ONCOPROTEINS IN TUMOR EXTRACELLULAR MATRIX

(71) Applicant: CASE WESTERN RESERVE UNIVERSITY, Cleveland, OH (US)

(72) Inventors: Zheng-Rong Lu, Cleveland, OH (US); Songqi Gao, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 637 days.

This patent is subject to a terminal disclaimer.

(21) Appl. No.: 17/424,104

(22) PCT Filed: Jan. 17, 2020

(86) PCT No.: PCT/US2020/014110

§ 371 (c)(1),
(2) Date: Jul. 19, 2021

(87) PCT Pub. No.: WO2020/150617

PCT Pub. Date: Jul. 23, 2020

(65) Prior Publication Data

US 2022/0160903 A1 May 26, 2022

Related U.S. Application Data

(60) Provisional application No. 62/793,789, filed on Jan. 17, 2019.

(51) Int. Cl.
*A61K 51/04* (2006.01)
*A61K 51/08* (2006.01)

(52) U.S. Cl.
CPC ........ *A61K 51/0474* (2013.01); *A61K 51/088* (2013.01)

(58) Field of Classification Search
CPC .... A61K 51/00; A61K 51/04; A61K 51/0474; A61K 51/08; A61K 51/088
USPC .......... 424/1.11, 1.65, 1.69, 1.81, 1.85, 1.89, 424/9.1, 9.2; 530/300, 329; 514/1, 1.1, 514/21.4; 534/7, 10–16
See application file for complete search history.

(56) References Cited

U.S. PATENT DOCUMENTS 10,124,073 B2 * 11/2018 Lu ........................ A61K 51/082
10,653,801 B2 * 5/2020 Lu ...................... A61K 49/0056
10,925,980 B2 * 2/2021 Lu .......................... A61K 49/14
11,738,099 B2 * 8/2023 Lu ...................... A61K 49/0056
424/9.341

FOREIGN PATENT DOCUMENTS

WO 2018/215627 A1 11/2018

OTHER PUBLICATIONS

Ye et al, ACS Omega Publication, vol. 2, pp. 2459-2468 (Year: 2017).*
Chinese Office Action dated Mar. 31, 2023.
Chinese Application No. 2020800218382 Search Report.
Han, Zheng, et al. "Preparation and Evaluation of ZD2 Peptide 64Cu-DOTA Conjugate as a Positron Emission Tomography Probe for Detection and Characterization of Prostate Cancer", ACS Omega 2019, 4, 1185-1190.
Chinese Application No. 202080021838.2, Office Action dated Aug. 17, 2023.
European Application No. 20741042.4, Extended Search Report dated Jan. 2, 2023.
Han, Zheng, et al., Targeting Fibronectin for Cancer Imaging and Therapy, J Mater Chem B Mater Biol Med. Jan. 28, 2017: 5(4): 639-654.
De Leon-Rodriguez, Luis M., The Synthesis and Chelation Chemistry of DOTA-Peptide Conjugates, Feb. 2008, vol. 19, No. 2, 391-402.
Yin Zhang: "Positron Emission Tomography Imaging of CD105 Expression with a 64Cu-Labeled Monoclonal Antibody: NOTA Is Superior to DOTA", Plos One, vol. 6, No. 12, Dec. 9, 2011 (Dec. 9, 2011), p. e28005.
Sangeeta Ray Banerjee et al: "Preclinical Comparative Study of 68 Ga-Labeled DOTA, NOTA, and HBED-CC Chelated Radiotracers for Targeting PSMA", Bioconjugate Chemistry, vol. 27, No. 6, Jun. 15, 2016 (Jun. 15, 2016), pp. 1447-1455.
European Application No. 20741042.4, Office Action dated May 27, 2024.
Chinese Application No. 202080021838.2, Office Action dated Jan. 3, 2024.
Japanese Application No. 2021-541620, Office Action dated Jan. 9, 2024.
Japanese Application No. 2021-541620, Decision of Rejection dated Sep. 10, 2024.
Korean Application No. 10-2021-7025921, Office Action dated Sep. 17, 2025.
Canadian Application No. 3,127,188, Office Action dated Aug. 19, 2025.
Australian Application No. 2020208492, Examination Report dated Aug. 15, 2025.

* cited by examiner

*Primary Examiner* — D. L. Jones
(74) *Attorney, Agent, or Firm* — Tarolli, Sundheim, Covell & Tummino LLP

(57) ABSTRACT

A PET/SPECT probe includes the following formula:

P-L-C wherein P is a EDB-FN targeting peptide, C is a PET/SPECT contrast agent; and L is an optional linker that covalently links the peptide to the contrast agent.

13 Claims, 15 Drawing Sheets

Specification includes a Sequence Listing.

Fig. 6
Solid phase
peptide synthesis
: resin
(1)
(1) DIPEA/DMF, HBTU,
Fmoc-NH-(CH2)3-COOH
(2) 20% Piperidine
(2)
(1) DIPEA/DMF, HBTU
(2) TFA/H2O/TIS
(3)
68GaCl3
Acetate buffer, pH 5.5
(4)

PEPTIDE PET/SPECT PROBES SPECIFIC TO ONCOPROTEINS IN TUMOR EXTRACELLULAR MATRIX

RELATED APPLICATION

This application claims priority from U.S. Provisional Application No. 62/793,789, filed Jan. 17, 2019, the subject matter of which is incorporated herein by reference in its entirety.

GOVERNMENT FUNDING

This invention was made with government support under CA211762 and CA194518, awarded by The National Institutes of Health. The government has certain rights in the invention.

BACKGROUND

Cancer detection and treatment are hindered by the inability to differentiate between cancer cells and normal cells. Better detection tools for cancer or tumor imaging are needed for earlier diagnosis of cancers. Molecular recognition of tumor cells would facilitate guided surgical resection. In order to improve surgical resection, targeted imaging tools must specifically label tumor cells, not only in the main tumor but also along the edge of the tumor and in the small tumor cell clusters that disperse throughout the body. Targeted imaging tools designed to label molecules that accumulate in the tumor microenvironment may also be advantageous as therapeutic targeting agents, as they can identify both the main tumor cell population and areas with infiltrating cells that contribute to tumor recurrence. The ability to directly target the tumor cell and/or its microenvironment would increase both the specificity and sensitivity of current treatments, therefore reducing non-specific side effects of chemotherapeutics that affect cells throughout the body.

Positron emission tomography (PET) imaging has been applied in the clinical examination of prostate cancer mainly with [$^{18}$F]-FDG, based on elevated glucose metabolism of prostate cancer compared to that of normal tissues. However, [$^{18}$F]-FDG PET has not demonstrated the ability to differentiate benign prostate cancer from aggressive ones. PSMA-specific PET probes have recently been developed for prostate cancer. Clinical studies have demonstrated the ability of the PSMA probes for effective detection of PSMA-positive prostate tumors. However, a recent study cautioned that the PSMA probes may not be able to differentiate benign tissues from prostate cancer. PET probes are needed to detect and risk-stratify aggressive cancer to meet the clinical need of a noninvasive diagnostic modality for precision clinical management of cancer.

SUMMARY

Embodiments described herein relate to peptide positron emission tomography (PET)/single photon emission computed tomography (SPECT) probes to oncoproteins in tumor and/or cancer extracellular matrix that can be used to detect the location and/or distribution of cancer in tissue of a subject, the aggressiveness of cancer in a subject, and/or the efficacy of a cancer therapeutic and/or cancer therapy administered to a subject in need thereof.

In some embodiments, the PET/SPECT probe can include the following formula:

P-L-C wherein P is a peptide that includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 19, SEQ ID NO: 20, SEQ ID NO: 21, SEQ ID NO: 22, SEQ ID NO: 23, SEQ ID NO: 24; and retro-inverso amino acid sequences thereof, C is a PET or SPECT contrast agent; and L is an optional linker that covalently links the peptide to the PET/SPECT contrast agent.

In some embodiments, the linker is a non-peptide linker. The non-peptide linker can be a non-peptide aliphatic, heteroaliphatic, cyclic, and/or heterocyclic linker. The non-peptide linker can include, for example, an alkylene, alkylene oxide, arylene, or alkylenearylene linker that covalently links the peptide and contrast agent.

The PET/SPECT contrast agent can include at least one of a metal chelating agent or a metallofullerene and positron or gamma emitting radionuclides. The metal chelating agent can include, for example, at least one of diethylenetriaminepentaacetate (DTPA), 1,4,7,10-tetraazadodecanetetraacetate (DOTA), 1,4,7,10-tetraazadodecane-1,4,7-triacetate (DO3A), ethylenediaminetetraacetate (EDTA), 1,4,7,10-tetraazacyclotridecanetetraacetic acid (TRITA), 1,4,8,11-tetraazacyclotetradecane-1,4,8,11-tetraacetic acid (TETA), 1,4,7,10-tetraazadodecanetetramethylacetate (DOTMA), 1,4,7,10-tetraazadodecane-1,4,7-trimethylacetate (DO3MA), N,N',N",N'"-tetraphosphonatomethyl-1,4,7,10-tetraazacyclododecane (DOTP), 1,4,7,10-tetraazacyclododecane-1,4,7,10-tetrakis(methylene methylphosphonic acid) (DOTMP), 1,4,7,10-tetraazacyclododecane-1,4,7,10-tetrakis(methylene phenylphosphonic acid) (DOTPP), N,N'-ethylenedi-L-cysteine, 1,4,7-triazacyclononane-1,4,7-triacetic acid (NOTA), 1,4,7-triazacyclononane (TACN), N,N'Bis(2-hydroxy-5-(ethylene-beta-carboxy)benzyl)ethylenediamine N,N'-diacetic acid (HBED-CC), and derivatives thereof. The positron or gamma emitting radionuclide can include, for example, $^{67}$Ga, $^{68}$Ga, $^{64}$Cu, $^{99m}$Tc, $^{111}$In, $^{89}$Zr, $^{90}$Y, $^{153}$Sm, or $^{89}$Sr.

In some embodiments, the PET/SPECT probe can have the formula:

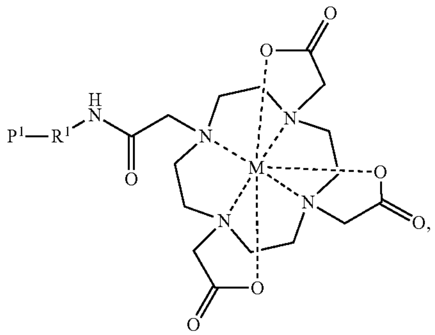

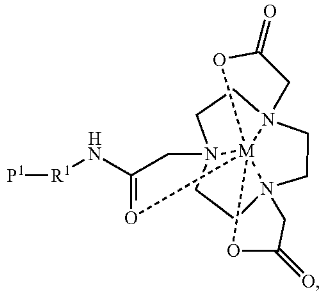

or

-continued

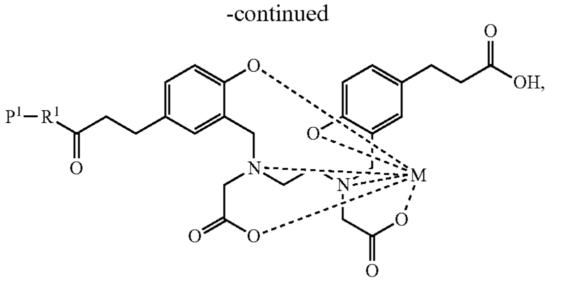

wherein:

- $P_1$ includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 19, SEQ ID NO: 20, SEQ ID NO: 21, SEQ ID NO: 22, SEQ ID NO: 23, SEQ ID NO: 24, and retro-inverso amino acid sequences thereof;
- $R^1$ is optional and when present can include an alkylene, alkylene oxide, arylene, or alkylenearylene linker, such as $-(CH_2)_n-$, $-(OCH_2CH_2)_n$, or an arylene, where n is an integer from 1 to 18; and
- M is a metal selected from the group consisting of $^{67}Ga$, $^{68}Ga$, 64Cu, $^{99m}Tc$, $^{111}In$, $^{89}Zr$, $^{90}Y$, $^{153}Sm$, or $^{89}Sr$; or salts thereof.

In still other embodiments, the PET/SPECT probe can be administered systematically to the subject to detect the distribution and/or location of cancer in the subject as well as the cancer aggressiveness. The cancer can include, for example, at least one of breast cancer, liver cancer, stomach cancer, colon cancer, pancreatic cancer, ovarian cancer, lung cancer, kidney cancer, prostate cancer, testicular cancer, glioblastoma, sarcoma, bone cancer, brain cancer, head and neck cancers, or skin cancer.

DETAILED DESCRIPTION

Figure 1:
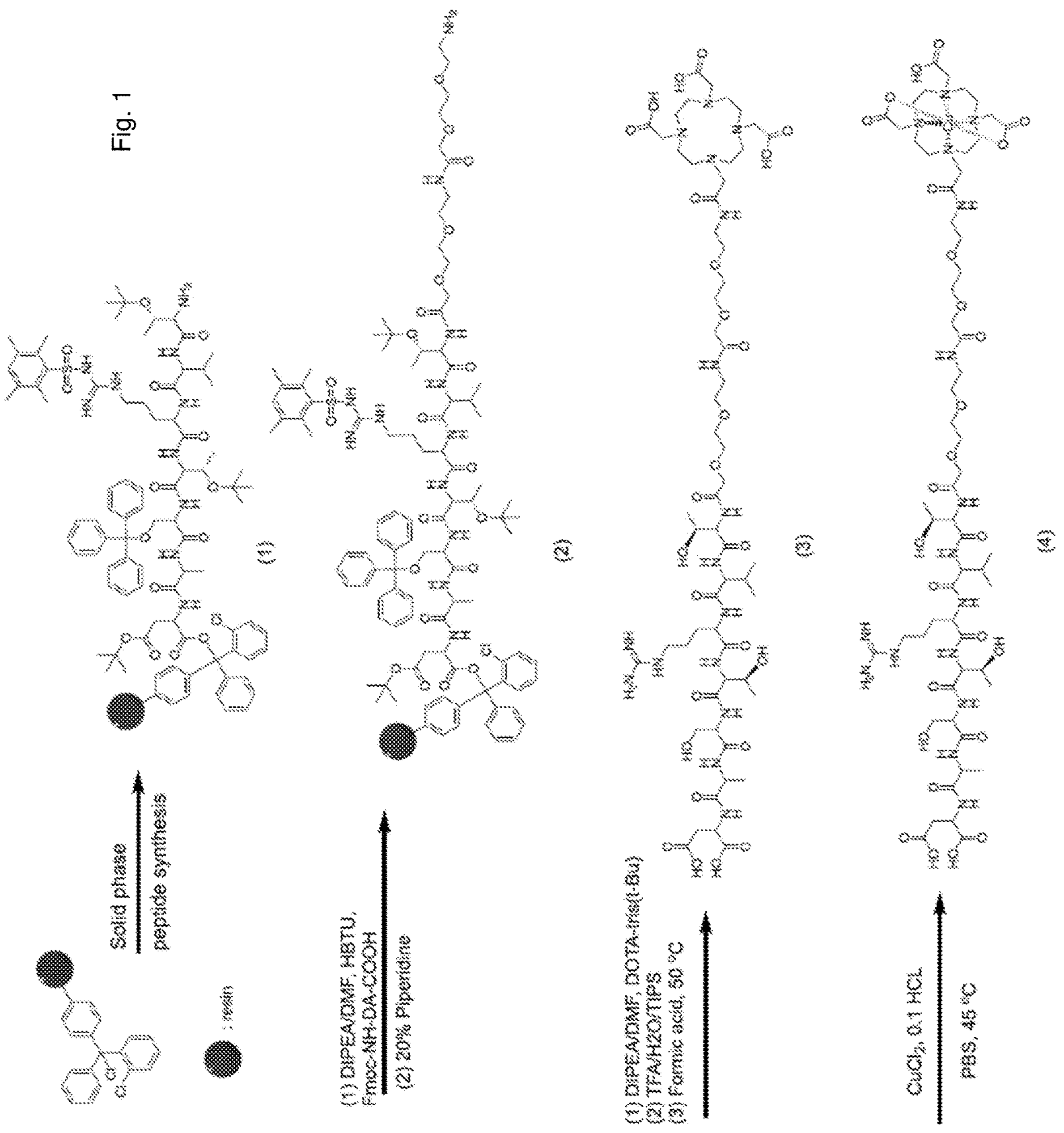
FIG. 1 illustrates a schematic showing the synthesis of ZD2-DA-($^{64}$Cu-DOTA).

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular,* 5th Edition, Springer-Verlag: New York, 1991, and Lewin, *Genes V*, Oxford University Press: New York, 1994.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.," as used herein are non-limiting and are for illustrative purposes only. "Including" and "including but not limited to" are used interchangeably.

The term "or" as used herein should be understood to mean "and/or", unless the context clearly indicates otherwise.

The term "agent" is used herein to denote a chemical compound, a mixture of chemical compounds, a biological macromolecule, or an extract made from biological materials.

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

The terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, pancreatic carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

The term "isolated" as used herein with respect to nucleic acids, such as DNA or RNA, or amino acids refers to molecules separated from other DNAs, or RNAs, polypeptides or protein respectively, which are present in the natural source of the macromolecule. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" or "isolated peptide" is meant to include nucleic acid fragments or peptide fragments, which are not naturally occurring as fragments and would not be found in the natural state.

The term "nucleic acid" refers to polynucleotides, such as deoxyribonucleic acid (DNA), and, where appropriate, ribonucleic acid (RNA). The term should also be understood to include, as equivalents, analogs of RNA or DNA made from nucleotide analogs, and, as applicable to the embodiment being described, single (sense or antisense) and double-stranded polynucleotides.

The terms "polynucleotide sequence" and "nucleotide sequence" are also used interchangeably herein.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The terms "patient", "subject", "mammalian host," and the like are used interchangeably herein, and refer to mammals, including human and veterinary subjects.

The term "polypeptide" refers to a polymer composed of amino acid residues related naturally occurring structural variants, and synthetic non-naturally occurring analogs thereof linked via peptide bonds or modified peptide bonds (i.e., peptide isosteres), related naturally occurring structural variants, and synthetic non-naturally occurring analogs thereof, glycosylated polypeptides, and all "mimetic" and "peptidomimetic" polypeptide forms. Synthetic polypeptides can be synthesized, for example, using an automated polypeptide synthesizer. The term can refer to an oligopeptide, peptide, polypeptide, or protein sequence, or to a fragment, portion, or subunit of any of these. The term "protein" typically refers to large polypeptides. The term "peptide" typically refers to short polypeptides.

A "portion" of a polypeptide or protein means at least about three sequential amino acid residues of the polypeptide. It is understood that a portion of a polypeptide may include every amino acid residue of the polypeptide.

"Mutants," "derivatives," and "variants" of a polypeptide (or of the DNA encoding the same) are polypeptides which may be modified or altered in one or more amino acids (or in one or more nucleotides) such that the peptide (or the nucleic acid) is not identical to the wild-type sequence, but has homology to the wild type polypeptide (or the nucleic acid).

A "mutation" of a polypeptide (or of the DNA encoding the same) is a modification or alteration of one or more amino acids (or in one or more nucleotides) such that the peptide (or nucleic acid) is not identical to the sequences recited herein, but has homology to the wild type polypeptide (or the nucleic acid).

"Recombinant," as used herein, means that a protein is derived from a prokaryotic or eukaryotic expression system.

The phrases "systemic administration," "administered systemically," "peripheral administration" and "administered peripherally" as used herein mean the administration of a compound, agent or other material other than directly into a specific tissue, organ, or region of the subject being treated (e.g., brain), such that it enters the animal's system and, thus, is subject to metabolism and other like processes, for example, subcutaneous administration.

The term "wild type" refers to the naturally-occurring polynucleotide sequence encoding a protein, or a portion thereof, or protein sequence, or portion thereof, respectively, as it normally exists in vivo.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

Embodiments described herein relate to peptide positron emission tomography (PET)/single photon emission computed tomography (SPECT) probes to oncoproteins in tumor and/or cancer extracellular matrix that can be used for detecting, monitoring, and/or imaging cancer distribution and/or location and/or cancer cell metastasis, migration, and/or invasion in a subject, detecting and/or monitoring cancer cell aggressiveness and/or malignancy in a subject, and/or determining and/or monitoring the efficacy of a cancer therapeutic and/or cancer therapy administered to a subject in need thereof.

The PET/SPECT probes described herein include targeting peptides with a peptide sequence that specifically binds to and/or complexes with oncofetal fibronectin (onfFN) isoforms, extradomain-B fibronectin (EDB-FN) or extradomain-A (EDA-FN) fibronectin. Cancer and, particularly, malignant cancer has a unique tumor microenvironment that facilitates cancer cell survival, proliferation, and metastasis. The presence of onfFN has been found in various human cancer types, including prostate, breast and pancreatic cancer. High expression of onfFN, EDB-FN and/or EDA-FN correlated with cancer aggressiveness and inversely with patient survival. It was found that PET/SPECT probes that include targeting peptides, which specifically bind to EDB-FN and/or EDB-FN, can be used for detecting, monitoring, and/or imaging cancer cells in tissue of a subject as well as to determine cancer cell aggressiveness, malignancy, metastasis, migration, dispersal, and/or invasion.

PET/SPECT probes including the targeting peptides can be administered systemically to a subject, such as by intravenous or parenteral administration, and readily target the extracellular matrix proteins EDB-FN and/or EDA-FN to define cancer cell location, distribution, and/or aggressiveness as well as tumor cell margins in the subject.

In some embodiments, the PET/SPECT probe can include the following formula:

P-L-C wherein P is a targeting peptide C, is a PET/SPECT contrast agent; and L is an optional linker that covalently links the peptide to the contrast agent.

In some embodiments, the targeting peptide can specifically bind to EDB-FN. Targeting peptides that specifically bind EDB-FN can include linear peptides having the amino acid sequences of TVRTSAD (SEQ ID NO: 1), NWGDRIL (SEQ ID NO: 2), NWGKPIK (SEQ ID NO: 3), SGVKSAF (SEQ ID NO: 4), GVKSYNE (SEQ ID NO: 5), IGKTNTL (SEQ ID NO: 6), IGNSNTL (SEQ ID NO: 7), IGNTIPV (SEQ ID NO: 8), and LYANSPF (SEQ ID NO: 9), cyclic peptides having the amino acid sequences of CTVRTSADC (SEQ ID NO: 10), CNWGDRILC (SEQ ID NO: 11), CNWGKPIKC (SEQ ID NO: 12), CSGVKSAFC (SEQ ID NO: 13), CGVKSYNEC (SEQ ID NO: 14), CIGKTNTLC (SEQ ID NO: 15), CIGNSNTLC (SEQ ID NO: 16), CIGNTIPVC (SEQ ID NO: 17), or CLYANSPFC (SEQ ID NO: 18), linear peptides with cysteine linkers, or retro-inverso peptides having a retro-inverso amino acid sequence of the linear peptides thereof.

In other embodiments, the targeting peptide can specifically bind to EDA-FN. Targeting peptides that specifically bind EDA-FN can include linear peptides having the amino acid sequences of WNYPFRL (SEQ ID NO: 19), SNTSYVN (SEQ ID NO: 20), SFSYTSG (SEQ ID NO: 21), WSPAPMS (SEQ ID NO: 22), TREHPAQ (SEQ ID NO: 23), or ARIIDNA (SEQ ID NO: 24), cyclic peptides having the amino acid sequences of CWNYPFRLC (SEQ ID NO: 25), CSNTSYVNC (SEQ ID NO: 26), CSFSYTSGC (SEQ ID NO: 27), CWSPAPMSC (SEQ ID NO: 28), CTREHPAQC (SEQ ID NO: 29), or CARIIDNAC (SEQ ID NO: 30), linear peptides with cysteine linkers, or retro-inverso peptides having a retro-inverso amino acid sequence of the linear peptides thereof.

The targeting peptides can be subject to various changes, substitutions, insertions, and deletions where such changes provide for certain advantages in its use. In this regard, targeting peptides that bind to and/or complex with EDB-FN and/or EDA-FN can be substantially homologous with, rather than be identical to, the sequence of a recited peptide where one or more changes are made and it retains the ability to function as specifically binding to and/or complexing with EDB-FN and/or EDA-FN.

The targeting peptides can be in any of a variety of forms of polypeptide derivatives, that include amides, conjugates with proteins, cyclized polypeptides, polymerized polypeptides, retro-inverso peptides, analogs, fragments, chemically modified polypeptides, and the like derivatives.

Retro-inverso peptides are linear peptides whose amino acid sequence is reversed and the α-center chirality of the amino acid subunits is inverted as well. These types of peptides are designed by including D-amino acids in the reverse sequence to help maintain side chain topology similar to that of the original L-amino acid peptide and make them more resistant to proteolytic degradation. D-amino acids represent conformational mirror images of natural L-amino acids occurring in natural proteins present in biological systems. Peptides that contain D-amino acids have advantages over peptides that just contain L-amino acids. In general, these types of peptides are less susceptible to proteolytic degradation and have a longer effective time when used. Furthermore, the insertion of D-amino acids in selected sequence regions as sequence blocks containing only D-amino acids or in-between L-amino acids allows the design of targeting peptides that are bioactive and possess increased bioavailability in addition to being resistant to proteolysis. Furthermore, if properly designed, retro-inverso peptides can have binding characteristics similar to L-peptides.

The term “analog” includes any peptide having an amino acid residue sequence substantially identical to a sequence specifically shown herein in which one or more residues have been conservatively substituted with a functionally similar residue and that specifically binds to and/or complexes with EDB-FN and/or EDA-FN as described herein. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase “conservative substitution” also includes the use of a chemically derivatized residue in place of a non-derivatized residue provided that such peptide displays the requisite binding activity.

“Chemical derivative” refers to a subject peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Peptides described herein also include any peptide having one or more additions and/or deletions or residues relative to the sequence of a peptide whose sequence is shown herein, so long as the requisite binding specificity or activity is maintained.

The term “fragment” refers to any subject peptide having an amino acid residue sequence shorter than that of a polypeptide whose amino acid residue sequence is shown herein.

Any polypeptide or compound may also be used in the form of a pharmaceutically acceptable salt. Acids, which are capable of forming salts with the polypeptides, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the polypeptides include inorganic bases such as sodium hydroxide, ammonium hydroxide, potassium hydroxide and the like; and organic bases such as mono-, di- and tri-alkyl and arylamines (e.g., triethylamine, diisopropylamine, methylamine, dimethylamine and the like) and optionally substituted ethanolamines (e.g., ethanolamine, diethanolamine and the like).

The targeting peptides can be synthesized by any of the techniques that are known to those skilled in the polypeptide art, including recombinant DNA techniques. Synthetic chemistry techniques, such as a solid-phase Merrifield-type synthesis, can be used for reasons of purity, antigenic specificity, freedom from undesired side products, ease of production and the like. A summary of the many techniques available can be found in Steward et al., “Solid Phase Peptide Synthesis”, W. H. Freeman Co., San Francisco, 1969; Bodanszky, et al., “Peptide Synthesis”, John Wiley & Sons, Second Edition, 1976; J. Meienhofer, “Hormonal Proteins and Peptides”, Vol. 2, p. 46, Academic Press (New York), 1983; Merrifield, Adv. Enzymol., 32:221-96, 1969; Fields et al., int. J. Peptide Protein Res., 35:161-214, 1990; and U.S. Pat. No. 4,244,946 for solid phase peptide synthesis, and Schroder et al., “The Peptides”, Vol. 1, Academic Press (New York), 1965 for classical solution synthesis, each of which is incorporated herein by reference. Appropriate protective groups usable in such synthesis are described in the above texts and in J. F. W. McOmie, “Protective Groups in Organic Chemistry”, Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

Furthermore, the targeting peptides described herein can be used as a starting point to develop higher affinity small molecules, peptides, antibodies, and/or antibody fragments with similar ligand binding capabilities. The development and screening of small molecules from pharmacophores of the peptides using, for example, in silico screening, can be readily performed, and the binding affinity of such identified molecules can be readily screened against targeting peptides using assays described herein to select small molecule agents.

Additional residues may also be added at either terminus of a peptide for the purpose of providing a “linker” by which the peptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject targeting peptide agent can differ by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

Where the linker is a peptide linker, the polypeptide-linker may be produced as a single recombinant polypeptide using a conventional molecular biological/recombinant DNA method.

For example, the targeting peptide can include lysines that can be capable of reacting with a carbonyl-containing group, such as an anhydride or an acid halide, or with an alkyl group containing a good leaving group (e.g., a halide). The targeting peptide can also include cysteines that facilitate chemical coupling via thiol-selective chemistry (e.g., maleimide-activated compounds). Further, the targeting peptides can include tyrosines, which can be modified using diazonium coupling reactions. In an exemplary embodiment, the amino acid residue linker is a cysteine-glycine (CG) linker.

In other embodiments, a chemical binder group can be used. A binder group can serve to increase the chemical reactivity of a substituent on either the targeting peptide or the compound or molecule to which the targeting peptide is bound, and thus increase the coupling efficiency. Binder chemistries can include maleimidyl binders, which can be used to bind to thiol groups, isothiocyanate and succinimidyl (e.g., N-hydroxysuccinimidyl (NHS)) binders, which can bind to free amine groups, diazonium which can be used to bind to phenol, and amines, which can be used to bind with free acids such as carboxylate groups using carbodiimide activation.

Useful functional groups are present on the targeting peptides based on the particular amino acids present, and additional groups can be designed. It will be evident to those skilled in the art that a variety of bifunctional or polyfunctional reagents, both homo- and hetero-functional (such as those described in the catalog of the Pierce Chemical Co., Rockford, Ill.), can be employed as a binder group. Coupling can be effected, for example, through amino groups, carboxyl groups, sulfhydryl groups or oxidized carbohydrate residues.

Other types of binding chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide binder wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to peptides are described by U.S. Pat. No. 7,666, 624.

In some embodiments, the linker is a non-peptide linker. The non-peptide linker can be a non-peptide aliphatic, heteroaliphatic, cyclic, and/or heterocyclic linker. The non-peptide linker can include, for example, an alkylene, alkylene oxide, arylene, or alkylenearylene linker that covalently links the peptide and contrast agent.

In other embodiments, the linker can be a PEG molecule linker. The PEG molecules can have a variety of lengths and molecular weights, including, for example, PEG 200, PEG 1000, PEG 1500, PEG 4600, PEG 10,000, or combinations thereof.

The PET/SPECT contrast agent can be conjugated directly to the targeting peptide or be linked to the targeting peptide via the linker. The role of the contrast agent is to facilitate the detection step of a detection or diagnostic method by allowing visualization of the complex formed by binding of a PET/SPECT probe comprising a targeting peptide to EDB-FN and/or EDA-FN. The contrast agent can be selected such that it generates a signal, which can be measured and whose intensity is related (preferably proportional) to the amount of the PET/SPECT probe bound to the tissue being analyzed.

In certain embodiments, the contrast agent includes a chelating agent and a metal ion. The chelating agent generally possesses one or more groups capable of forming a covalent bond with the linker. A number of different chelating agents known in the art can be used herein. In one aspect, the chelating agent comprises an acyclic or cyclic compound comprising at least one heteroatom (e.g., oxygen, nitrogen, sulfur, phosphorous) that has lone-pair electrons capable of coordinating with the imaging agent. The metal chelating agent can include, for example, at least one of diethylenetriaminepentaacetate (DTPA), 1,4,7,10-tetraazadodecanetetraacetate (DOTA), 1,4,7,10-tetraazadodecane-1,4,7-triacetate (DO3A), ethylenediaminetetraacetate (EDTA), 1,4,7,10-tetraazacyclotridecanetetraacetic acid (TRITA), 1,4,8,11-tetraazacyclotetradecane-1,4,8,11-tetraacetic acid (TETA), 1,4,7,10-tetraazadodecanetetramethylacetate (DOTMA), 1,4,7,10-tetraazadodecane-1,4,7-trimethylacetate (DO3MA), N,N',N'',N'''-tetraphosphonatomethyl-1,4,7,10-tetraazacyclododecane (DOTP), 1,4,7,10-tetraazacyclododecane-1,4,7,10-tetrakis(methylene methylphosphonic acid) (DOTMP), 1,4,7,10-tetraazacyclododecane-1,4,7,10-tetrakis(methylene phenylphosphonic acid) (DOTPP), N,N'-ethylenedi-L-cysteine, 1,4,7-triazacyclononane-1,4,7-triacetic acid (NOTA), 1,4,7-triazacyclononane (TACN), N,N'Bis(2-hydroxy-5-(ethylene-beta-carboxy)benzyl)ethylenediamnine N,N'-diacetic acid (HBED-CC), and derivatives thereof. The term "derivative" is defined herein as the corresponding salt and ester thereof of the chelating agent.

The selection of the metal ion can vary depending upon the detection technique (e.g., PET or SPECT). Metal ions useful in PET and SPECT imaging can include $^{67}$Ga, $^{68}$Ga, $^{64}$Cu, $^{99m}$Tc, $^{111}$In, $^{89}$Zr, $^{90}$Y, $^{153}$Sm, or $^{89}$Sr.

In some embodiments, the PET/SPECT probe can have the formula:

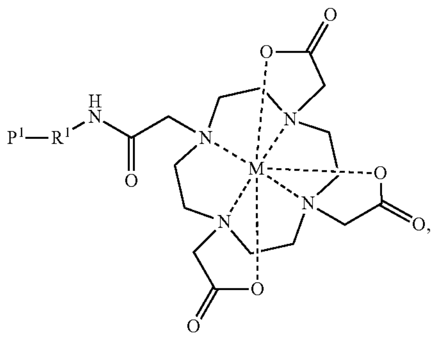

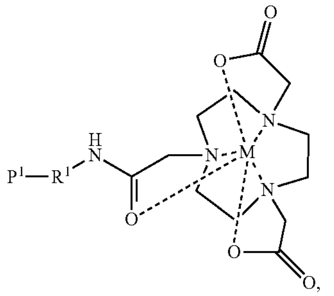

or

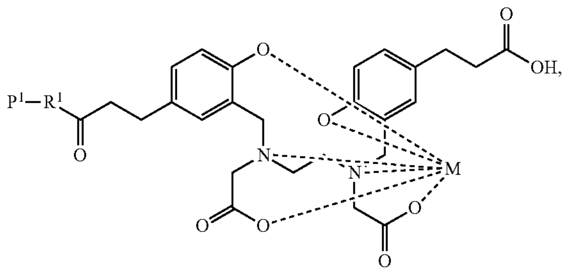

wherein:

$P_1$ includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:

9, WNYPFRL (SEQ ID NO: 19), SNTSYVN (SEQ ID NO: 20), SFSYTSG (SEQ ID NO: 21), WSPAPMS (SEQ ID NO: 22), TREHPAQ (SEQ ID NO: 23), ARIIDNA (SEQ ID NO: 24), and retro-inverso amino acid sequences thereof;

$R^1$ is optional and if present includes an alkylene, alkylene oxide, arylene, or alkylenearylene linker, such as $-(CH_2)_n-$, $-(OCH_2CH_2)_n$, or an arylene, where n is an integer from 1 to 18; and M is a metal selected from the group consisting of $^{67}Ga$, $^{68}Ga$, 64Cu, $^{99m}Tc$, $^{111}In$, $^{89}Zr$, $^{90}Y$, $^{153}Sm$, or $^{89}Sr$; or salts thereof.

In other embodiments, the PET/SPECT probe can have the formula:

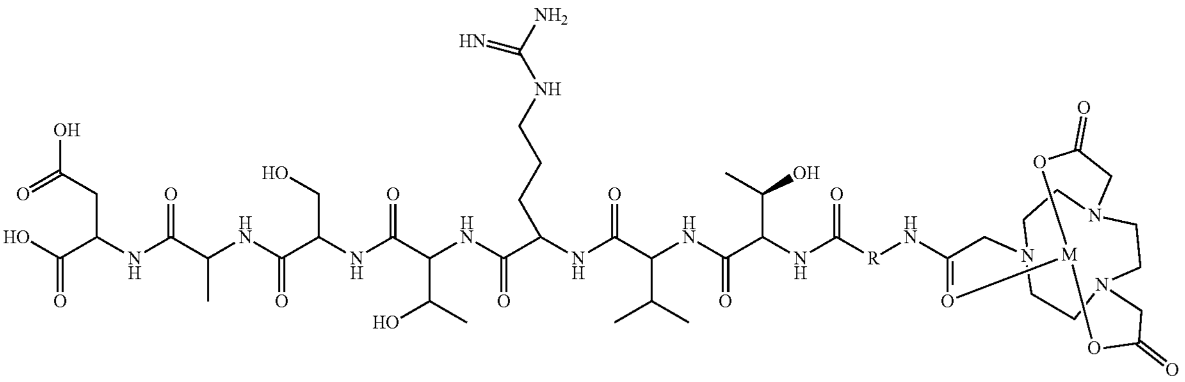

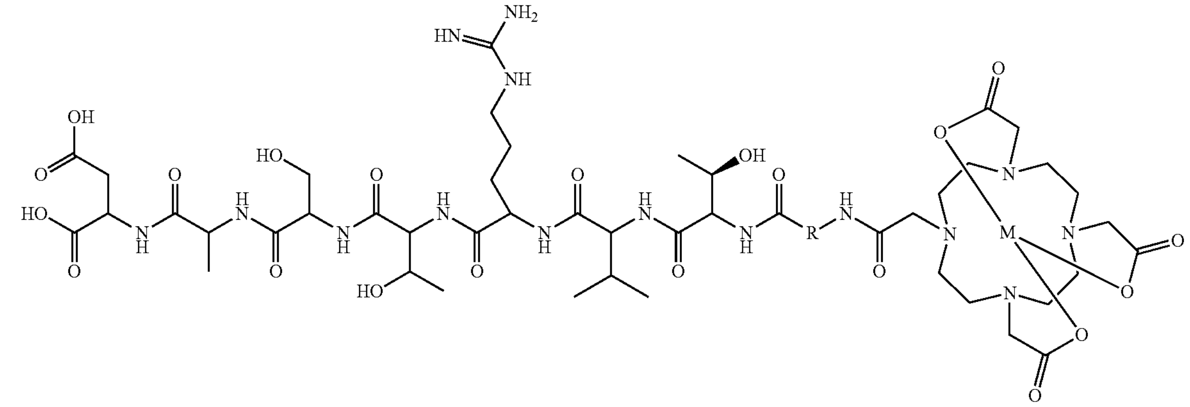

R = $(CH_2)n$, $(OCH_2CH_2)n$, 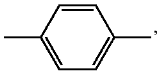, or any other spacer n = 1-18

M = $^{67}Ga$, $^{68}Ga$, $^{64}Cu$, $^{99m}Tc$, $^{111}In$, $^{89}Zr$, $^{90}Y$, $^{153}Sm$, $^{89}Sr$,

In still still other embodiments, the PET/SPECT probe can have the formula:

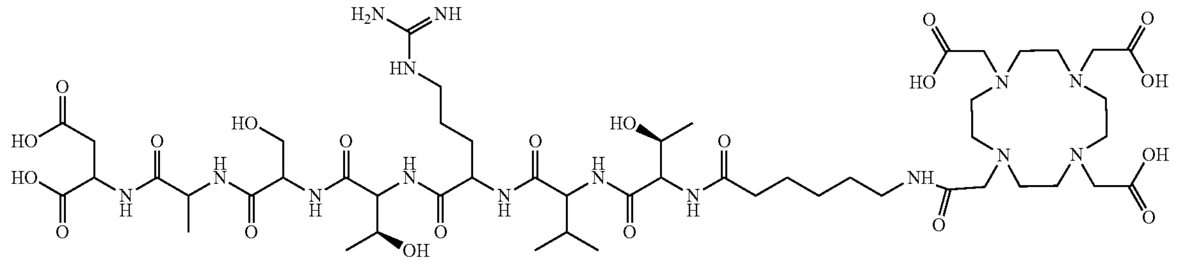

ZD2-DOTA

-continued

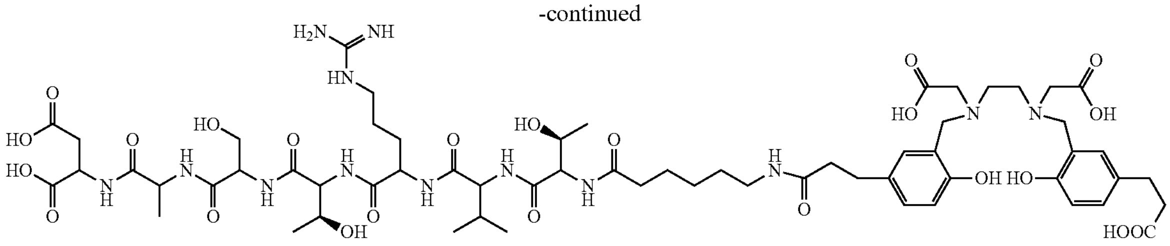

ZD2-HBED-CC and a PET/SPECT radionuclide selected from the group consisting of $^{67}Ga$, $^{68}Ga$, $^{64}Cu$, $^{99m}Tc$, $^{111}In$, $^{89}Zr$, $^{90}Y$, $^{153}Sm$, or $^{89}Sr$; or salts thereof.

The PET/SPECT probe described herein can be administered to the subject by, for example, systemic, topical, and/or parenteral methods of administration. These methods include, e.g., injection, infusion, deposition, implantation, or topical administration, or any other method of administration where access to the tissue by the molecular probe is desired. In one example, administration of the molecular probe can be by intravenous injection of the molecular probe in the subject. Single or multiple administrations of the probe can be given. "Administered", as used herein, means provision or delivery of a molecular probe in an amount(s) and for a period of time(s) effective to label cancer cells in the subject.

PET/SPECT probes comprising the targeting peptides described herein can be administered to a subject in a detectable quantity of a pharmaceutical composition containing a molecular probe or a pharmaceutically acceptable water-soluble salt thereof, to a patient.

A "detectable quantity" means that the amount of the molecular probe that is administered is sufficient to enable detection of binding or complexing of the probe to EDB-FN and/or EDA-FN expressed by the cancer cells or other cells in the cancer cell microenvironment. An "imaging effective quantity" means that the amount of the PET/SPECT probe that is administered is sufficient to enable imaging of binding or complexing of the molecular probe to the EDB-FN and/or EDA-FN of the cancer cells or other cells in the cancer cell microenvironment.

Formulation of the PET/SPECT probe to be administered will vary according to the route of administration selected (e.g., solution, emulsion, capsule, and the like). Suitable pharmaceutically acceptable carriers may contain inert ingredients which do not unduly inhibit the biological activity of the compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. Formulation will vary according to the route of administration selected (e.g., solution, emulsion, capsule).

Any polypeptide or compound may also be used in the form of a pharmaceutically acceptable salt. Acids, which are capable of forming salts with the polypeptides, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the polypeptides include inorganic bases, such as sodium hydroxide, ammonium hydroxide, potassium hydroxide and the like; and organic bases such as mono-, di- and tri-alkyl and arylamines (e.g., triethylamine, diisopropylamine, methylamine, dimethylamine and the like) and optionally substituted ethanolamines (e.g., ethanolamine, diethanolamine and the like).

The PET/SPECT probes described herein can be used in a method to detect and/or determine the presence, location, and/or distribution of cancer cells expressing EDB-FN and/or EDA-FN, in an organ, tissue, or body area of a subject. The presence, location, and/or distribution of the probe in the animal's tissue, e.g., prostate tissue, can be visualized (e.g., with an in vivo imaging modality described above). "Distribution" as used herein is the spatial property of being scattered about over an area or volume. In this case, "the distribution of cancer cells" is the spatial property of cancer cells being scattered about over an area or volume included in the animal's tissue, e.g., prostate tissue. The distribution of the molecular probe may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject.

In one aspect, the PET/SPECT probes may be administered to a subject to assess the distribution of malignant or metastatic cancer cells in a subject and correlate the distribution to a specific location. Surgeons routinely use stereotactic techniques and intra-operative MRI (iMRI) in surgical resections. This allows them to specifically identify and sample tissue from distinct regions of the tumor such as the tumor edge or tumor center. Frequently, they also sample regions of tissue on the tumor margin that are outside the tumor edge that appear to be grossly normal but are infiltrated by dispersing tumor cells upon histological examination.

PET/SPECT probes that specifically bind to and/or complex with EDB-FN and/or EDA-FN associated with malignant or metastatic cells can be used in intra-operative imaging techniques to guide surgical resection and eliminate the "educated guess" of the location of the tumor margin by the surgeon. Previous studies have determined that more extensive surgical resection improves patient survival. Thus, probes that function as diagnostic molecular imaging agents have the potential to increase patient survival rates.

In some embodiments, to identify and facilitate removal of cancers cells, microscopic intra-operative imaging (IOI) techniques can be combined with systemically administered or locally administered PET/SPECT probes described herein. The PET/SPECT probe upon administration to the subject can target and detect and/or determine the presence, location, and/or distribution of cancer cells, i.e., cancer cells associated with EDB-FN and/or EDA-FN expression, in an organ or body area of a patient. In one example, the probe can be combined with IOI to identify malignant cells that have infiltrated and/or are beginning to infiltrate at a tumor margin. The method can be performed in real-time during surgery. The method can include local or systemic application of the PET/SPECT probe that includes a detectable moiety, such as a PET or SPECT contrast agent. An imaging modality can then be used to detect and subsequently gather image data. The resultant image data may be used to determine, at least in part, a surgical and/or radiological treatment. Alternatively, this image data may be used to control, at least in part, an automated surgical device (e.g., laser, scalpel, micromachine) or to aid in manual guidance of surgery. Further, the image data may be used to plan and/or control the delivery of a therapeutic agent (e.g., by a micro-electronic machine or micro-machine).

Another embodiment described herein relates to a method of determining the aggressiveness or malignancy of cancer cells in a subject. It was found that the binding intensity of the PET/SPECT probes to a cancer correlated with the cancer aggressiveness. Enhanced binding correlated with more aggressive cancer whereas lower or reduced binding correlated with less aggressive or benign tumors. In one example, binding of the probe to prostate tumor sections correlated with to Gleason score based on tumor aggressiveness, where enhanced binding intensity of the molecular probe correlated to aggressive or malignant prostate cancer and which was distinguished from benign prostatic hyperplasia, which displayed lower binding intensity of the probe. The methods and molecular probes described herein can be used to monitor and/or compare the aggressiveness a cancer in a subject prior to administration of a cancer therapeutic or cancer therapy, during administration, or post therapeutic regimen.

Another embodiment described herein relates to a method of monitoring the efficacy of a cancer therapeutic or cancer therapy administered to a subject. The methods and PET/SPECT probes described herein can be used to monitor and/or compare the aggressiveness, invasion, migration, dispersal, and metastases of a cancer in a subject prior to administration of a cancer therapeutic or cancer therapy, during administration, or post therapeutic regimen.

A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy. This can provide a direct clinical efficacy endpoint measure of a cancer therapeutic. Therefore, in another aspect, a method of monitoring the efficacy of a cancer therapeutic is provided. More specifically, embodiments of the application provide for a method of monitoring the efficacy of a cancer therapy.

The method of monitoring the efficacy of a cancer therapeutic can include the steps of administering in vivo to the animal a PET/SPECT probe as described herein, then visualizing a distribution of the probe in the animal (e.g., with an in vivo imaging modality as described herein), and then correlating the distribution of the probe with the efficacy of the cancer therapeutic. It is contemplated that the administering step can occur before, during, and after the course of a therapeutic regimen in order to determine the efficacy of a chosen therapeutic regimen. One way to assess the efficacy of the cancer therapeutic is to compare the distribution of a probe pre and post cancer therapy.

In some embodiments, the PET/SPECT probe bound to and/or complexed with the EDB-FN and/or EDA-FN is detected in the subject to detect and/or provide the aggressiveness, location and/or distribution of the cancer cells in the subject. The aggressiveness, location and/or distribution of the cancer cells in the subject can then be compared to a control to determine the efficacy of the cancer therapeutic and/or cancer therapy. The control can be the location and/or distribution of the cancer cells in the subject prior to the administration of the cancer therapeutic and/or cancer therapy. The location and/or distribution of the cancer cells in the subject prior to the administration of the cancer therapeutic and/or cancer therapy can be determined by administering the probe to the subject and detecting the probe bound to and/or complexed with cancer cells in the subject prior to administration of the cancer therapeutic and/or cancer therapy.

In certain embodiments, the methods and PET/SPECT probes described herein can be used to measure the efficacy of a therapeutic administered to a subject for treating a metastatic or aggressive cancer. In this embodiment, the probe can be administered to the subject prior to, during, or post administration of the therapeutic regimen and the distribution of cancer cells can be imaged to determine the efficacy of the therapeutic regimen. In one example, the therapeutic regimen can include a surgical resection of the metastatic cancer and the probe can be used to define the distribution of the metastatic cancer pre-operative and post-operative to determine the efficacy of the surgical resection. Optionally, the methods and probes can be used in an intra-operative surgical procedure, such as a surgical tumor resection, to more readily define and/or image the cancer cell mass or volume during the surgery.

In other embodiments, the targeting peptides can be conjugated to a therapeutic agent and administered to a subject for treating a cancer, such as a metastatic cancer. In this embodiment, the targeting peptides conjugated to the therapeutic agent can be administered to the subject and the metastatic cells can be targeted with the therapeutic agent.

The therapeutic agent can include an anti-proliferative agent that exerts an antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

In some embodiments, the targeting peptides can be coupled to the therapeutic agent using a linking molecule. The linking molecule may be a linker. Alternatively, a linking molecule may be a non-peptide linker.

EXAMPLES

Example 1

We developed a ZD2 $^{64}$Cu-DOTA conjugate as a PET probe for EDB-FN and evaluated its efficacy for PET imaging in mice bearing aggressive PC3 and slow-growing LNCaP human prostate tumor xenografts. We showed that EDB-FN was highly expressed in aggressive PC3 tumors and negligibly expressed in slow-growing and non-metastatic LNCaP tumors. MRI with a EDB-FN targeted contrast agent ZD2-Gd(HP-DO3A) showed stronger contrast enhancement in the PC3 tumors than in the LNCaP tumors. The use of $^{64}$Cu is particularly attractive because of its 12.74 h half-life, providing extended imaging time frame for cancer detection in the prostate with minimal background inference, especially from the bladder. The PET probe was synthesized by conjugating the ZD2 peptide to a macrocyclic ligand, DOTA, followed by complexation with $^{64}CuCl_2$. The ability of the PET probe in cancer detection and characterization of tumor aggressiveness was evaluated in mice bearing PC3 and LNCaP tumors.

Materials and Methods

Synthesis of ZD2-PEG-DOTA and Chelates

The reagents used for chemical synthesis were purchased from Sigma-Aldrich (Saint Louis, MO, USA), unless otherwise stated. Fmoc-protected amino acids and 2-chlorotrityl chloride resin were acquired from Chem-Impex International, Inc. (Wood Dale, IL). The spacer, Fmoc-8-amino-3,6-dioxaocta-noic acid (Fmoc-NH—$(CH_2CH_2O)_2$—$CH_2COOH$), was acquired from Chempep (Wellington, FL). 1,4,7,10-Tetraaza-cyclododecane-1,4,7-tris-tert-butyl acetate-10-acetic acid (DOTA-tris(t-Bu)) was purchased from TCI America (Port-land, OR).

The precursor ZD2-DA-DOTA, which contains the ZD2 peptide (sequence: TVRTSAD), two repeats of $NH_2$—$(CH_2CH_2O)_2$—$CH_2COOH$, and DOTA was synthesized by sequentially adding the corresponding protected amino acids, Fmoc-NH—$(CH_2CH_2O)_2$—$CH_2COOH$, and t-Bu-DOTA on the resin in a solid phase using standard Fmoc-peptide chemistry. The product was then cleaved off the resin using trifluoroacetic acid/triisopropyl silane/$H_2O$ (96.5:1:2.5) and stirred at room temperature for 3 h and precipitated in ether to give a crude product. The final product was purified using preparative HPLC on an Agilent 1100 HPLC system equipped with a semipreparative C18 column (Agilent Technologies, Santa Clara, CA). ZD2-PEG-DOTA was characterized by MALDI-TOF mass spectrometry on a Voyager DE-STR spectrometer (PerkinElmer, Waltham, MA) in the linear mode with R 2,5-dihydroxybenzoic acid as a matrix (M+1: 1425.8, observed; 1425.7, calculated).

Cell Culture and Animal Models

The animal study has been approved by the Institutional Animal Care and Use Committee of the Case Western Reserve University (CWRU), and all subjects signed an informed consent form. PC3 and LNCaP cells were acquired from the American Type Culture Collection (ATCC, Manassas, VA, USA) and cultured in Roswell Park Memorial Institute medium (Thermo Fisher Scientific, Waltham, MA) supplemented with 10% fetal bovine serum, 100 U/mL penicillin, and 0.1 mg/mL streptomycin in a humid incubator maintained at 37° C. and 5% $CO_2$. Male athymic nude mice (4-6 weeks old) were acquired from the Case Comprehensive Cancer Center (Cleveland, OH, USA) and housed in the CWRU Animal Core Facility. Three million cells in high concentration Matrigel (Corning, Tewksbury, MA) were used for tumor inoculation. LNCaP cells were subcutaneously inoculated in the left flank of the mice. Four weeks later, PC3 cells were inoculated on the right flank of the same mice for PET imaging.

Radiolabeling

The radioisotope $^{64}$Cu(II) was acquired from the University of Wisconsin-Madison (Madison, WI). The chelation of ZD2-PEG-DOTA with Cu(II) was first tested with cold $CuCl_2$ in 0.1 N HCl aqueous solution under the same condition as radiolabeling. Equal molar ZD2-DA-DOTA in PBS buffer (pH 7.4) and $CuCl_2$ solution was mixed and stirred at 45° C. for 30 min. The formation of ZD2-DA-(Cu-DOTA) was verified by MALDI-TOF mass spectrometry (M+1: 1487.8, observed; 1486.04, calculated). For radiolabeling, 10 mCi $^{64}$Cu(II) was dissolved in 200 μL of 0.1 N HCl. Twenty microliters of $^{64}$Cu(II) solution (ca. 1 mCi) was mixed with 480 μL of ZD2-DA-DOTA (0.05 mg/mL, a large excess, PBS) in a 1.5 mL microcentrifuge tube. The vessel was then maintained by heating at 45° C. for 30 min with intermittent shaking. The final pH of the solution was adjusted to be neutral using NaOH solution before injection.

PET Imaging

All in vivo imaging studies were conducted according to the CWRU Animal Research Committee-approved protocols and guidelines. The mice were anesthetized with 2% isoflurane in oxygen and injected with about 200 ρCi [about 7.4 MBq] ZD2-DA-$^{64}$Cu(DOTA) via the tail vein. The mice underwent 10 min static PET scans after 4 and 22 h uptake period PET scans (Inveon microPET, Siemens Medical Solutions USA Inc.). Images were reconstructed using 3D-OSEM with 3D histogramming and a zoom factor of 1.0 (two iterations followed by MAP with 18 iterations). CT scans (Siemens Medical Solutions USA Inc.) were performed after PET procedures for anatomical coregistration. AMIDE version 1.0.557 and AMIRA software were used to analyze the PET/CT images g. ROIs were drawn for PC3 and LNCaP tumors to calculate the ratio of specific to nonspecific (muscle) binding.

Biodistribution

After the last micro-PET/CT imaging at 22 h postinjection, three mice were euthanized, the organs and blood were collected and weighed, and the activity was determined in a gamma counter. The percent-injected dose per gram of tissue was calculated using a standard containing 2% of the injected dose.

Histological Analysis

After image acquisitions, the mice were euthanized. The tumors were harvested, embedded in an optimal cutting temperature medium, frozen in −80° C., cryosectioned at 5 μm, and permeabilized with cold acetone. The tissue was blocked with bovine serum albumin (1%) in PBS at room temperature for 1 h. Anti-EDB-FN BC1 antibody (Abcam, Cambridge, MA) was incubated with the tissue section of PC3 and LNCaP tumors. After extensive washing, secondary anti-mouse Alexa Fluor 488 antibody was incubated for 1 h. Tissue sections were counterstained with Prolong Gold antifade mounting medium with 4' 6-diamidino-2-phenylindole (Thermo Fisher, Waltham, MA). The stained tissues were imaged on an Olympus FV1000 confocal laser scanning microscope.

Results

The ZD2 $^{64}$Cu-DOTA conjugate was synthesized by conjugating ZD2 peptide to a macrocyclic chelate DOTA using solid-phase peptide chemistry, followed by complexation with $^{64}$CuCl2 (FIG. 1). A short spacer with two repeats of 8-amino-3,6-dioxaoctanoic acid was introduced between the peptide and the chelator. The targeted ligand ZD2-DA-DOTA was purified by preparative high-performance liquid chromatography (HPLC) and characterized by matrix-assisted laser desorption ionization time-of-flight (MALDI-TOF) mass spectrometry [m/z=1425.8 (M+1), observed; 1425.5, calculated]. The preparation of the targeted PET probe was demonstrated by complexation of equal molar ZD2-DA-DOTA in phosphate-buffered saline (PBS) buffer (pH 7.4) and cold $CuCl_2$ in dilute HCl (0.1 N) at 45° C. for 30 min, the same condition used for radiolabeling. The formation of ZD2-DA-(Cu-DOTA) was verified by MALDI-TOF mass spectrometry [m/z=1487.8 (M+1), observed; 1486.04, calculated].

The efficacy of ZD2-DA-($^{64}$Cu-DOTA) for prostate cancer PET imaging was then investigated in male nude mice bearing both PC3 and LNCaP human prostate cancer xenografts. Previously, we showed that EDB-FN was highly expressed in aggressive PC3 tumors and negligibly expressed in slow-growing and nonmetastatic LNCaP tumors. The tumor models were used to represent high-risk and low-risk prostate tumors and to test the ability of the probe to detect and stratify aggressive prostate cancer. Radiolabeling was performed by mixing 20 μL of $^{64}$Cu(II) solution (0.1 N HCl, ca. 1 mCi or 37 MBq) with 480 μL of ZD2-DA-DOTA (0.05 mg/mL, a large excess, PBS, pH=7.4) in a 1.5 mL microcentrifuge tube and was maintained at 45° C. for 30 min with intermittent shaking. The reaction mixture was then diluted in the ratio of 1:2 with PBS and tested with a pH paper to ensure neutral pH for intravenous injection. The radiotracer was injected intra-venously at the dose of 7.4 MBq (200 μCi) per mouse. PET images of the mice were acquired in a group of four mice bearing both PC3 and LNCaP tumor xenografts at 4 and 22 h after the injection.

Figure 2:
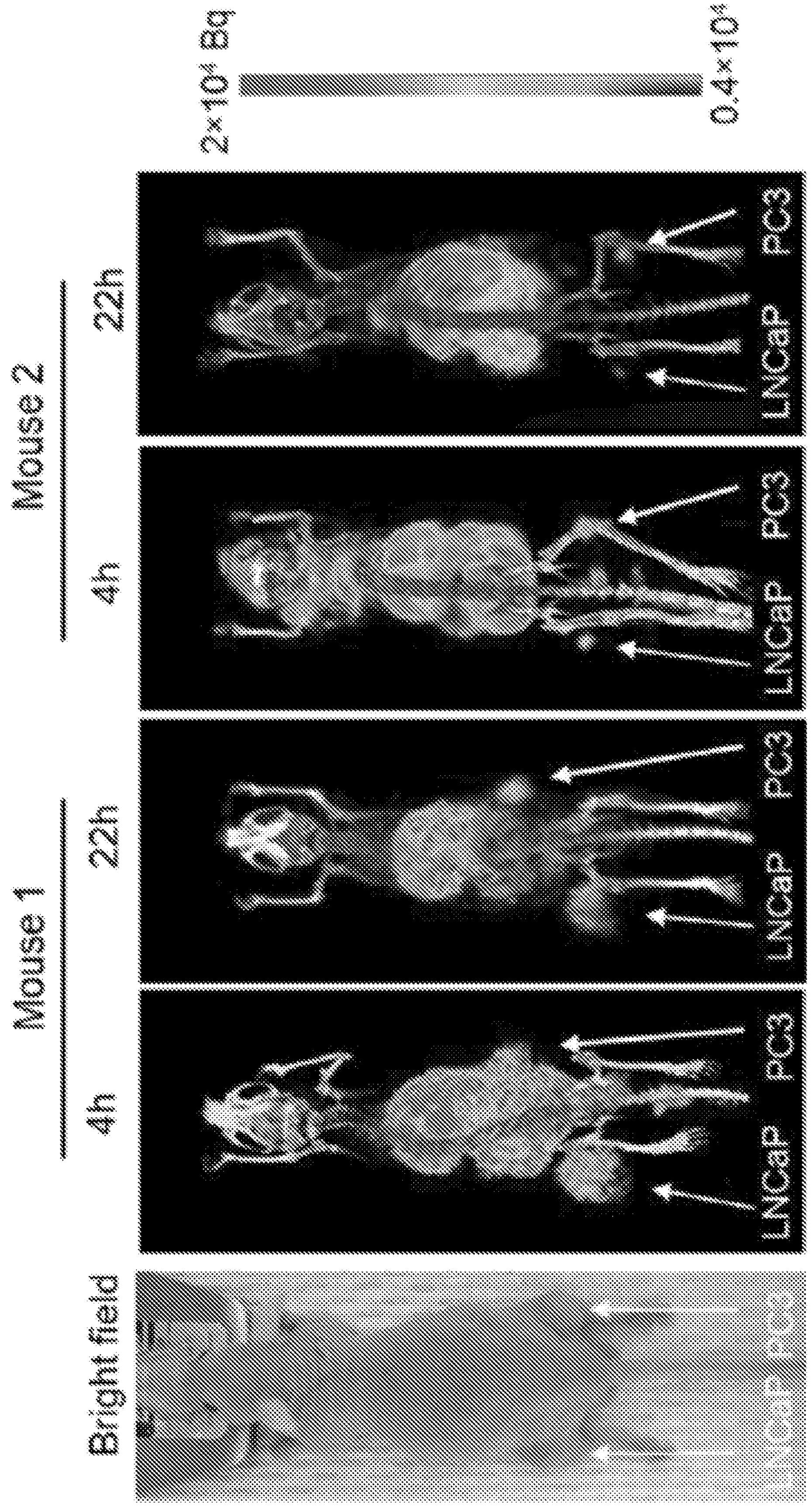
FIG. 2 illustrates macroscopic bright-field and 3D volume rendering PET/CT images of two representative mice bearing LNCaP and PC3 tumors at 4 and 22 h after injection of ZD2-DA-($^{64}$Cu-DOTA).
Figure 3:
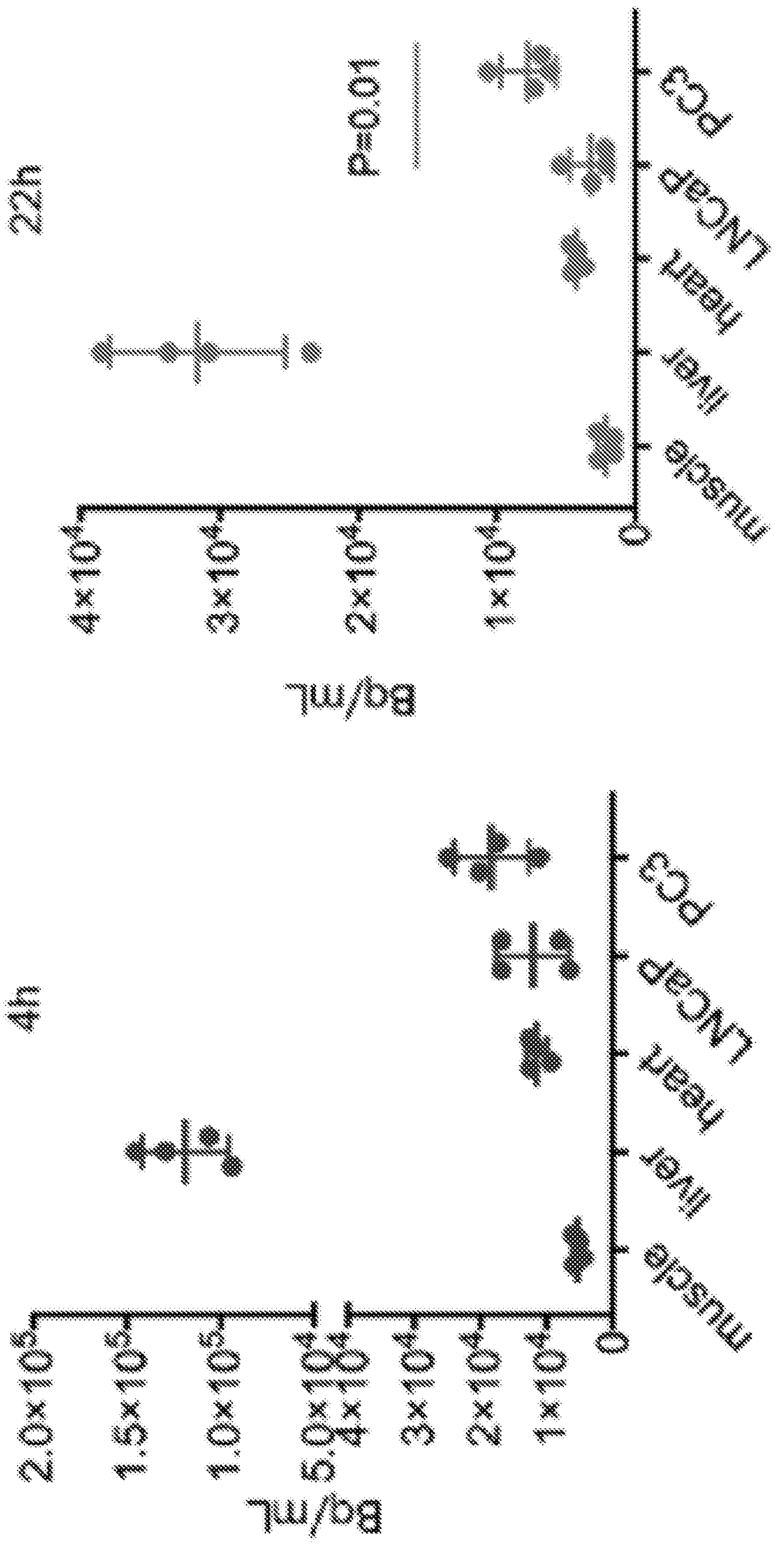
FIG. 3 illustrates quantitative tracer uptake in the muscle, liver, heart, and LNCaP and PC3 tumors at 4 and 22 h after ZD2-DA-$^{64}$Cu(DOTA) injection (N=4).

FIG. 2 shows the representative three-dimensional (3D) volume rendering and axial PET/computed tomography (CT) images of two tumor-bearing mice at 4 and 22 h after injection of ZD2-DA-($^{64}$Cu-DOTA). Stronger signal was visible in the aggressive PC3 tumors than in the slow-growing LNCaP tumors. The location and size of PC3 tumors were clearly delineated in the PET images. The tracer uptake or signal intensity was quantitatively analyzed in the region of interest (ROI) at 4 and 22 h. As shown in FIG. 3, ZD2-DA-($^{64}$Cu-DOTA) resulted in higher probe uptake in PC3 tumors than in LNCaP tumors. At 22 h, PET revealed an over two-folds higher accumulation of PET tracer in highly aggressive PC3 tumors (7711±1994 Bq/mL) compared to the less aggressive LNCaP tumors (3213±1511 Bq/mL) (N=4, $P<0.05$, two-tailed Student's t test). Other organs that demonstrated substantial radiotracer uptake were liver, stomach, and kidney, indicating the clearance of the radiotracer through hepatic and renal pathways.

Figure 4:
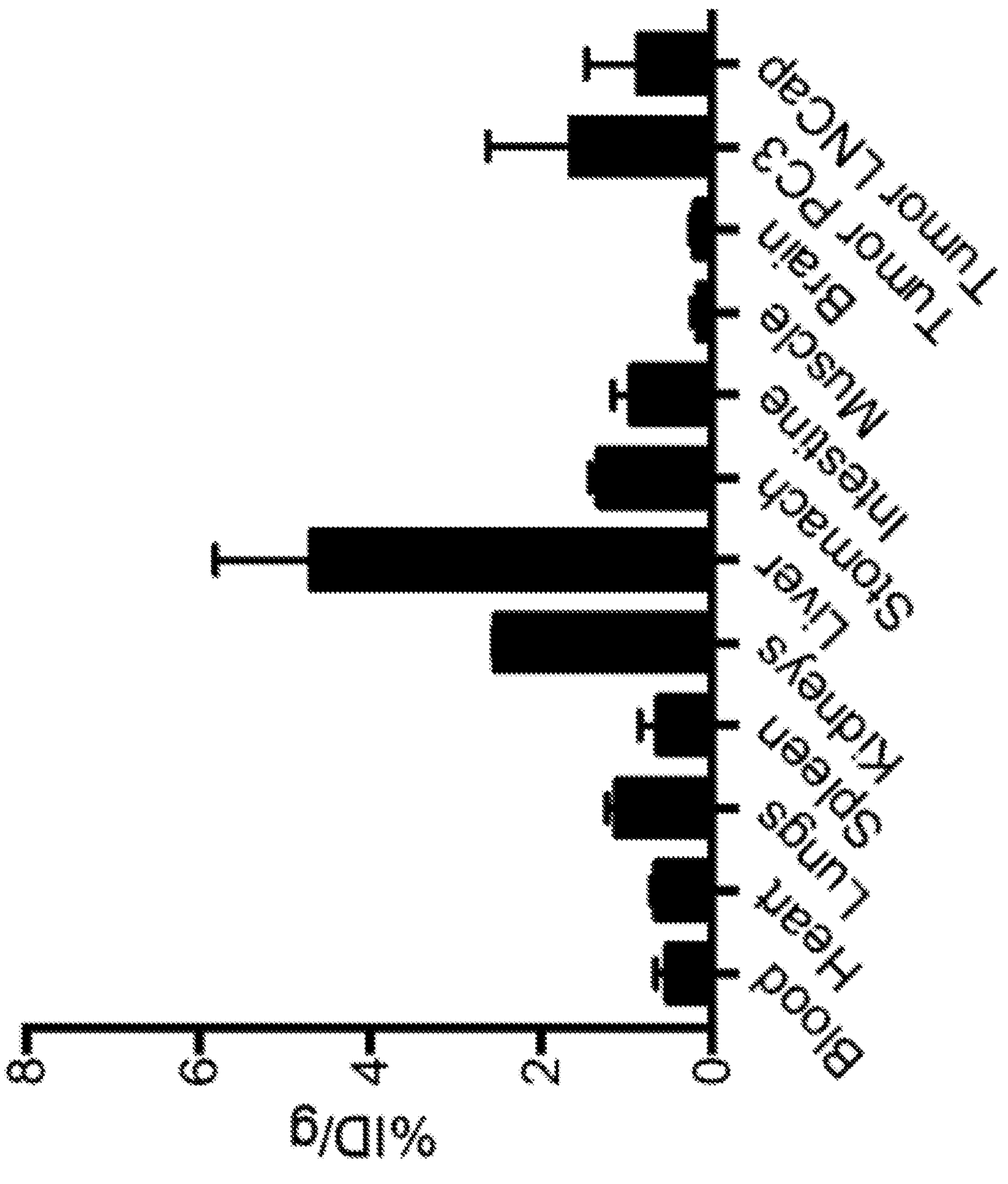
FIG. 4 illustrates graphs showing biodistribution of ZD2-DA-($^{64}$Cu-DOTA) in different tissues at 24 h after injection. Data is presented as mean±sem (N=3).

The biodistribution of the radiotracer was measured after scarifying the mice at 24 h post injection (FIG. 4). The biodistribution pattern was consistent with the findings in PET imaging, with a strong uptake in the tumors, liver, and kidney. Other organs, such as brain and muscle, exhibited a low radiotracer uptake, which is a desirable property of the radiotracer. Comparison of the radiotracer uptake in PC3 and LNCaP tumors indicated that the radiotracer accumulation in PC3 (1.$^{64}$ ID %/g) is higher than that in the LNCaP tumor (0.86 ID %/g) (N=3, P=0.32, two-tailed Student's t test), which corroborated that the probe preferentially accumulates in the more aggressive PC3 tumor than in the nonmetastatic LNCaP tumor.

Figure 5:
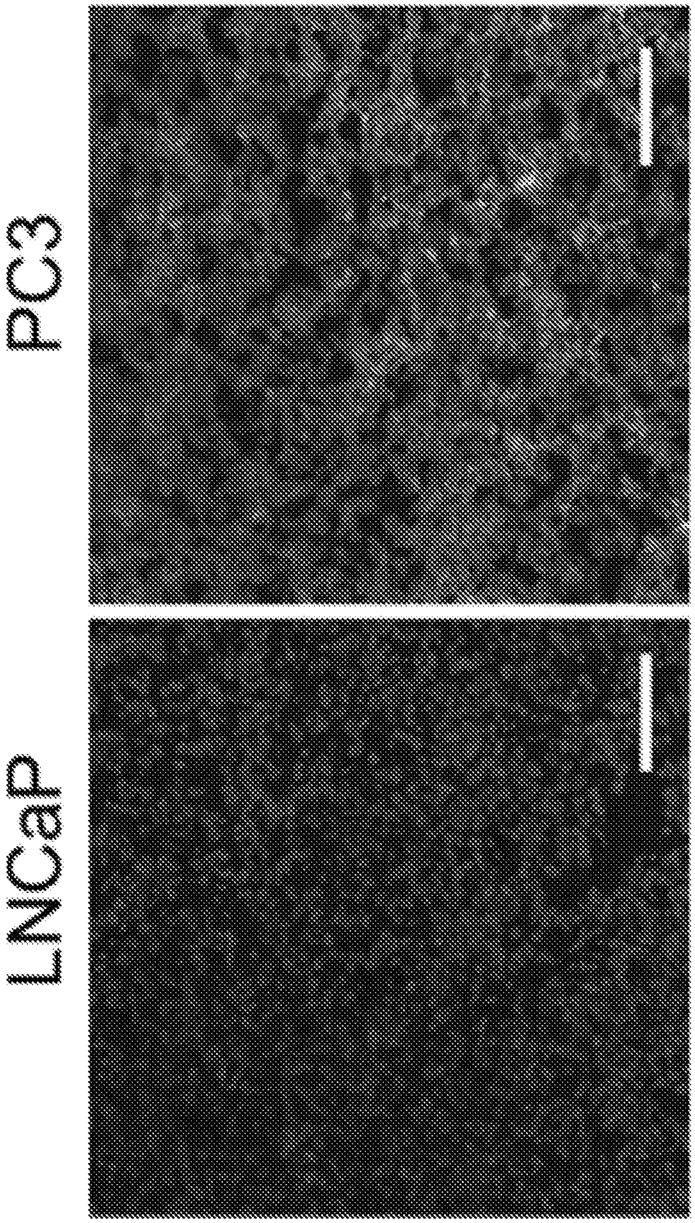
FIG. 5 illustrates images showing immunofluorescence staining of EDB-FN in LNCaP and PC3 prostate tumor sections. Scale bar: 50 μm.

The expression of EDB-FN in the prostate tumors was determined by immunofluorescence staining of the tissue section of PC3 and LNCaP tumors with an anti-EDB-FN monoclonal antibody BC1 after PET imaging. An Alexa Fluor 488-conjugated anti-mouse antibody was used to stain the BC1 antibody and EDB-FN. FIG. 5 shows the fluorescence images of the tumor sections acquired with an Olympus FV1000 confocal laser scanning microscope. Strong fluorescence staining was visible in the PC3 tumor section, whereas little staining was observed in the LNCaP tumor. Consistently, we have previously shown that the EDB mRNA level in LNCaP cells was lower than that in PC3 cells. The EDB-FN expression levels in two different prostate tumors correlated well with the observation with PET molecular imaging. The result suggests that ZD2-DA-($^{64}$Cu-DOTA) is effective for sensitive and quantitative visualization of EDB-FN expression in prostate cancer.

We showed in this Example, the potential of PET imaging of the ECM oncoprotein EDB-FN with a peptide probe ZD2-DA-($^{64}$Cu-DOTA) for detection and characterization of prostate cancer. Previously, we have shown that EDB-FN is highly expressed in the fast-growing PC3 tumors and lowly expressed in the slow-growing LNCaP tumors. ZD2 peptide-targeted MRI contrast agents were able to generate strong signal enhancement in PC3 tumors than in LNCaP tumors. The results of PET molecular imaging EDB-FN with ZD2-DA-($^{64}$Cu-DOTA), especially at 22 h post-injection, are in agreement with MR molecular imaging with a ZD2 peptide-targeted MRI contrast agent. When comparing the probe uptake in the tumors, stronger PET signals were detected in the fast-growing PC3 tumors with a high EDB- FN expression than in the slow-growing LNCaP tumors. However, a significant signal intensity was still observed in the LNCaP tumors of the PET images. This could be attributed to the relatively low chelation stability of $^{64}$Cu-DOTA monoamide. It has been shown that free $^{64}$Cu(II) released from the chelate could accumulate in the prostate tumors in animal models. The relatively high signal intensity in the LNCaP tumors could be attributed to the accumulation of free $^{64}$Cu(II) released from the probe. Nevertheless, the targeting effect of the ZD2 peptide of the probe still resulted in significantly higher signal intensity in the PC3 tumors than in the LNCaP tumors. As compared to MR molecular imaging, PET imaging produces sensitive and quantitative visualization and measurement of EDB-FN expression levels in prostate cancer, which provides more accurate risk stratification of aggressive prostate cancer.

Generally, PET imaging with probes of relatively short half-lives suffers from significant signal inference from the bladder for imaging primary tumors in the prostate because of a limited imaging window. The relatively long half-life $^{64}$Cu allows sufficient time to empty the bladder and to minimize the potential signal interference from the bladder, which is critical for early detection of primary tumors in the prostate. Substantial signals were still visible in tumors at 22 h post injection with little signals in the bladder. Significant signal intensity was observed in the liver with ZD2-DA-($^{64}$Cu-DOTA), which could also be attributed to the relatively low stability of Cu-DOTA monoamide. The release of free $^{64}$Cu-(II) from the chelate may lead to nonspecific accumulation of the radioisotope in the liver.

Antibodies and antibody fragments have been developed to target EDB-FN for the detection of cancer, including prostate cancer. This study showed that the small-peptide-targeted PET probe specific to EDB-FN also has the potential for prostate cancer imaging. As compared to antibody-based probes, small-peptide PET probes possess several advantages, including cost-effective production, better tumor penetration through diffusion and perfusion, and rapid excretion of the unbound probe from circulation.

Example 2

We showed that EDB-FN is highly expressed in human pancreatic cancer (PaCa) specimens and PaCa tissues from mouse PaCa models, with no expression in normal pancreatic tissues in either scenario. The presence of EDB-FN in PaCa tumor ECM will allow rapid and specific binding of a targeted tracer for sensitive molecular imaging and PaCa diagnosis. The peptide sequence of the EDB fragment is conserved in all mammalian species.

We identified a peptide ZD2 (Thr-Val-Arg-Thr-Ser-Ala-Asp) with specific binding to EDB-FN. ZD2 peptide exhibited strong binding affinity toward high-grade prostate tumor, weak binding affinity to low-grade tumor, and non-binding in normal tissue. In this Example, we show ZD2 peptide can be used to develop PET probes for sensitive and quantitative molecular imaging of EDB-FN for accurate detection and risk-stratification of pancreatic cancer. We have designed and synthesized a ZD2 peptide targeted Ga(III) PET probe by conjugating NOTA to ZD2 Peptide using a linker 6-aminohexanoic acid. We evaluated the efficacy of the targeted Ga(III) tracer for PET imaging in male nude mice bearing aggressive and fast-growing PC3 and slow growing LNCaP prostate cancer xenografts.

Experimental

Materials

Protected amino acids for peptide synthesis were purchased from Novabiochem (Burlington, MA, USA). N,N-Diisopropylethylamine (DIPEA) was bought from MP Biomedical LLC (Santa Ana, CA, USA). O-Benzotriazole-N,N,N',N'-tetramethyl-uronium-hexafluorophosphate (HBTU) was purchased from Anaspec Inc (Fremont, CA, USA). Fmoc-6-aminohexanoic acid was purchased from Chem-IMPEX International (WD, IL, USA). t-Butyl bromoacetate was bought from Sigma-Aldrich (St. Louis, MO, USA). All other chemical reagents were purchased from Thermo Fisher. $^{1}$H-NMR spectra were acquired on a 500 MHz Varian Inova NMR spectrometer (vendor and address) using TMS as an internal standard. Matrix-assisted laser desorption/ionization time-of-flight (MALDI-TOF) mass spectra were obtained on a Voyager DE-STR spectrometer (PerSeptive BioSystems) in linear mode with 2, 5-dihydroxybenzoic acid as a matrix. Agilent 1100 with ZORBAX 300 SB-C18 column semi-preparative HPLC was used for purification of the ligand with the following conditions: eluent A, $H_2O$/TFA (0.1%); B, MeCN/TFA (0.1%); 0% B for 15 min, 0-50% B for 30 min, 50% B for 5 min, 50%-100% B for 2 min, 100% B for 5 min, flow rate 2 mL/min, UV-detection at 210 nm. Ga was obtained from a $^{68}$Ge/$^{68}$Ga generator (ITG isotope technologies Garching GmbH, Germany) eluted with 0.1M HCl.

Synthesis

Synthesis of 1,4-bis (tert-butoxycarbonylmethyl)-1,4,7-triazanonane 1,4,7-Triazacyclononane (1.5 g, 11.62 mmol) was dissolved in dry $CHCl_3$ (15 mL) in ice bath, tertbutyl bromoacetate (4.98 g, 25.56 mmol) in $CHCl_3$ (30 mL) was added slowly over 1.5 h. The mixture was stirred at room temperature for 24 h and the solvent was removed. The residual was treated with DI water (15 mL) and was adjusted to pH 3 by 1M HCl and extracted with ether (50 mL×2). The organic phase was removed and the aqueous phase was adjusted to pH 8-9 by 1 M NaOH and extracted with $CH_2Cl_2$ (25 mL×3) again. Finally, the organic phase was evaporated to give the product. Yield: 36%, $^{1}$H NMR (500 MHz, $CDCl_3$): δ=1.48 (s, 18H), 2.79 (s, 4H), 3.03-3.07 (m, 4H), 3.24 (s, 4H), 3.37 (s, 4H), 9.46 (s, H).

Synthesis of NOTA-bis(t-Bu ester)

1,4-Bis(tert-butoxycarbonylmethyl)-1,4,7-triazanonane (0.3 g, 0.84 mmol) and bromoacetic acid (0.415 g, 3 mmol) were dissolved in methanol (3 mL), $K_2CO_3$ (0.53 g, 3.84 mmol) in water (3 mL) was added. The mixture was stirred at room temperature overnight and concentrated. Then the residue was dissolved in water and was adjusted to pH 4 by 1M HCl. Water was removed by rotary evaporation, and the product was purified by flash chromatography (methanol: ethyl acetate 6.5:3.5). Yield: $^{64}$%, $^{1}$H NMR (500 MHz, $D_2O$): δ=1.48 (s, 18H), 2.84 (s, 4H), 3.08 (m, 4H), 3.35 (s, 4H), 3.47 (s, 4H).

Synthesis of ZD2-HA-NOTA

ZD2-HA was synthesized using solid phase chemistry. The mixture of 6-aminohexanoic acid (1.5 eq.), HBTU (1.5 eq.), DIPEA (1.5 eq.) in 10 mL dry DMF was added to the resin at the end of peptide synthesis (0.5 mmol peptide) and was shaken until ninhydrin didn't change color (Kaiser test). Then the resin was washed using DMF (10 mL×3) and DCM (10 mL×3). ZD2-HA was subsequently cleaved from the resin for 3 hours using a cocktail of TFA:$H_2O$:TIBS (96.5:2.5:1). ZD2-HA was precipitated in cold ethyl ether, centrifuged and lyophilized. The product was characterized by MALDI-TOF mass spectrometry: m/z calculated for [M], $C_{47}H_{83}N_{15}O_{18}$, 1146.25; found (M+$H^+$), 1147.56.

Synthesis of cold Ga-ZD2-HA-NOTA

To the solution of ZD2-HA-NOTA (0.11 g, 0.1 mmol) dissolved in 10 mL of NaAc-Ac buffer solution (0.1 M, pH 5.5) and $Ga(NO_3)_3$ (0.076 g, 0.3 mmol) was added. The solution was stirred for overnight at room temperature, and finally, the product was purified using preparative HPLC and lyophilized to afford a fluffy white powder. Yield: 43%. The product was characterized by MALDI-TOF mass spectrometry: m/z calculated for [M], $C_{47}H_{81}GaN_{15}O_{18}$, 1212.51; found (M+$H^+$), 1213.54.

Results and Discussion

Chemistry and Radiochemistry

Figure 6:
FIG. 6 illustrates a schematic showing the synthesis procedure of ZD2-(Ga-NOTA) (4).

The synthetic of ZD2-HA-NOTA was depicted in FIG. 6. NOTA-bis(t-Bu ester) was prepared from TACN as starting material by twice substitutions. Then the precursor ZD2-HA-NOTA has been successfully synthesized by conjugating with NOTA-bis(t-Bu ester) and ZD2-HA using solid-phase peptide and purified by RP-HPLC. The purified ZD2-HA-NOTA was characterized by MALDI-TOF (m/z=1147.56) and HPLC (purity: approx 98%). $^{Nat}$Ga-ZD2-HA-NOTA was also prepared and characterized by MALDI-TOF (m/z=1213.54) and RP-HPLC (purity: approx 96%).

Figure 7:
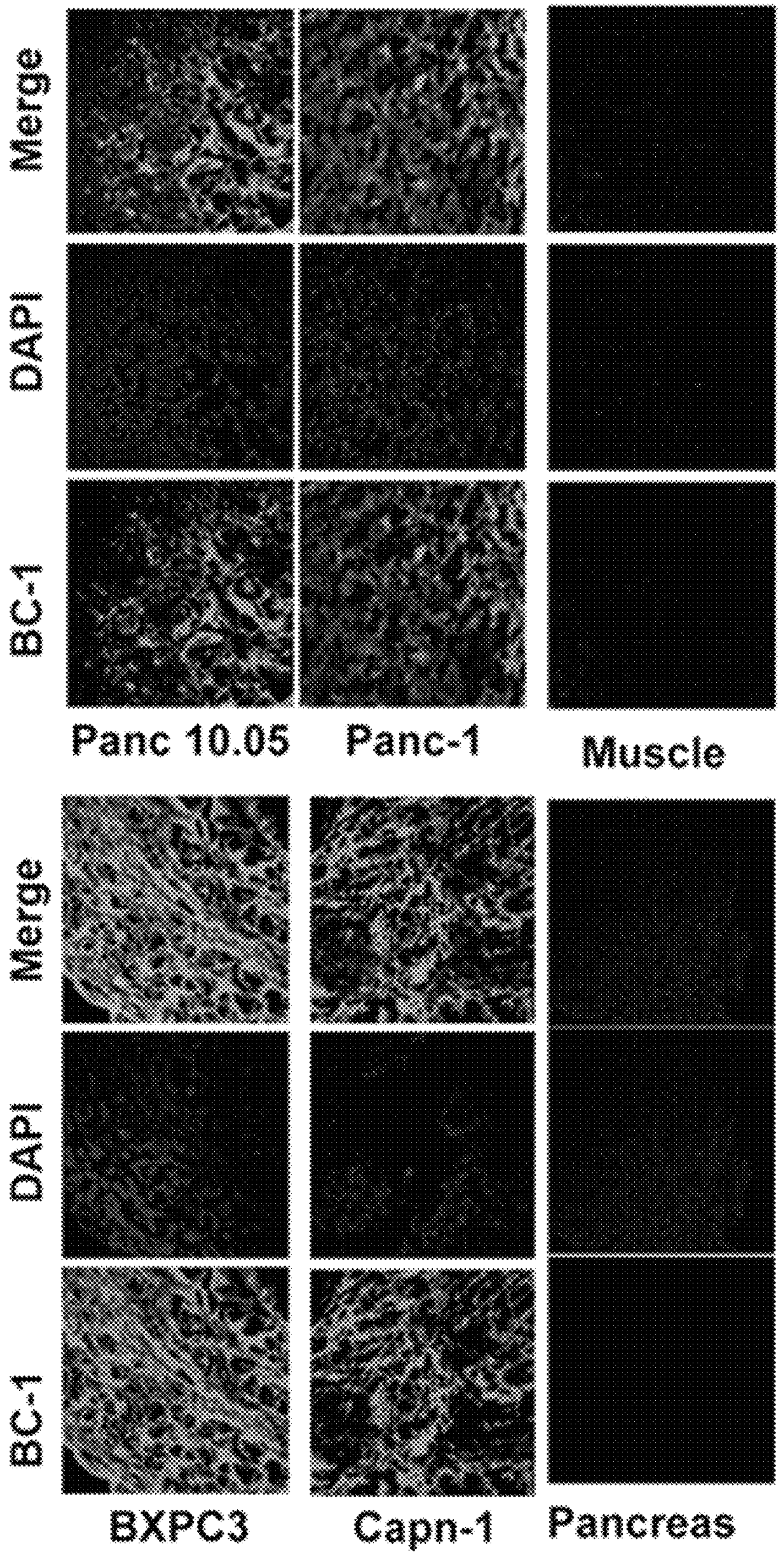
FIG. 7 illustrates western blots and fluorescence confocal images showing the expression of EDB-FN in BXPC3, Capan-1, Panc 10.05 and Panc-1 human pancreatic cancer cells and tumor xenografts in mice. The tissue slides are stained with BC-1 anti-EDB-FN monoclonal antibody and a secondary antibody labeled with AF-488 and DAPI.

A cold ZD2-(Ga-NOTA) was first synthesized according to the procedures depicted in FIG. 6. Macrocyclic ligand NOTA was used because it could readily form stable chelate with $^{68}$Ga(III) under relatively mild conditions, which is critical to reserve the binding property of the peptide. ZD2 peptide was synthesized using standard solid phase peptide synthesis and 6-aminohexanoic acid (HA) was then conjugated to the N-terminus of the peptide as a spacer. NOTA-bis(t-Bu ester) was finally conjugated to the amino group on the resin and the targeted ligand ZD2-NOTA was obtained by treating the resin with a cocktail of TFA:$H_2O$:TIBS (96.5:2.5:1). The final product was purified by preparative HPLC. The purified ZD2-NOTA was characterized by MALDI-TOF (m/z=1147.56 [M+1], obs.; 1146.25, calc.) with purity of approximately 98% (HPLC), FIG. 7A,B. ZD2-($^{Nat}$Ga-NOTA) was then prepared by reacting the ligand with an excess of $GaCl_3$ in acetate buffer (0.1 M, pH 5.5) at r.t. ZD2-($^{Nat}$Ga-NOTA) was purified using preparative HPLC and characterized by MALDI-TOF (m/z=1213.54 [M+1], obs.; 1212.51, calc.) with a purity of approximately 96% (HPLC), FIG. 43C,D. The peptide and ZD2-($^{Nat}$Ga-NOTA) are highly water-soluble, which is an advantageous feature for minimizing non-specific tissue binding.

Figure 8:
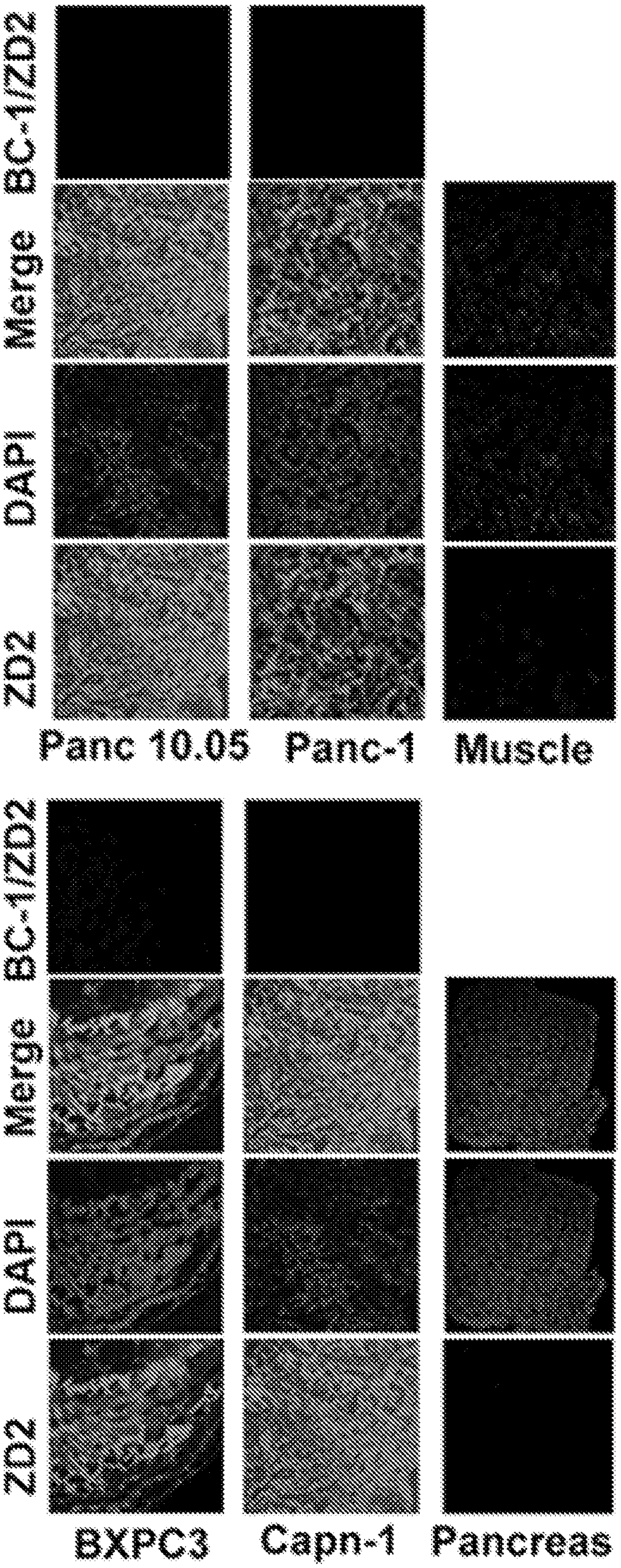
FIG. 8 illustrates images showing specific binding of ZD2-Cy5.5 to EDB-FN in BXPC3, Capan-1, Panc 10.05 and Panc-1 human pancreatic cancer xenografts specimens. The columns of BC-1/ZD2 show that the binding of ZD2-Cy5.5 was blocked by the pre-incubation of the specimens with BC-1 antibody.

The radioactive tracer ZD2-($^{68}$Ga-NOTA) was radiosynthesized by reacting ZD2-NOTA with $GaCl_3$ in sodium acetate buffer solution (0.1 M, pH 5.5) with at 90° C. for 15 min in the cGMP radiopharmaceutical lab of the University Hospitals, Cleveland (UH) in collaboration with Dr. Avril. The pH of the reaction solution was finally adjusted with NaOH. The radiochemical yield was about 77% as determined by HPLC equipped with a radiodetector and a Zorbax Eclipse C18 column (gradient of water+0.1% TFA/acetonitrile+0.1% TFA, UV at 220 nm). The radiolabeled tracer was purified using reverse phase HPLC with a C-18 column before imaging. The HPLC chromatograms of ZD2-($^{68}$Ga-NOTA) are shown in FIG. 8 and product parameters are summarized in Table 3. The small peaks around the main peak are commonly observed for radiolabeled peptide product possibly due to the complexation of $^{68}$Ga(III) with the peptide. The radiolabeling yield is comparable to that of the clinical tracers. The purity of the product is also equivalent to clinical grade products.

TABLE 3

Product specification of ZD2-($^{68}$Ga-NOTA)

| Parameter | ZD2-($^{68}$Ga-NOTA) |
|---|---|
| Precursor purity, % | 98 |
| RCY (n.d,c), % | 52 |
| RCY (d.c.), % | 77 |
| Product radioactivity (~14 mL final volume), mCi | 16.64 |
| Product radiopurity, % | 96.7 |
| Product UV-purity, % | 100 |
| pH | 7.5 |
| Immediate sterility | Passed |

Expression of EDB-FN in Human Pancreatic Cancer Cells and Tumor Xenografts

Figure 9:
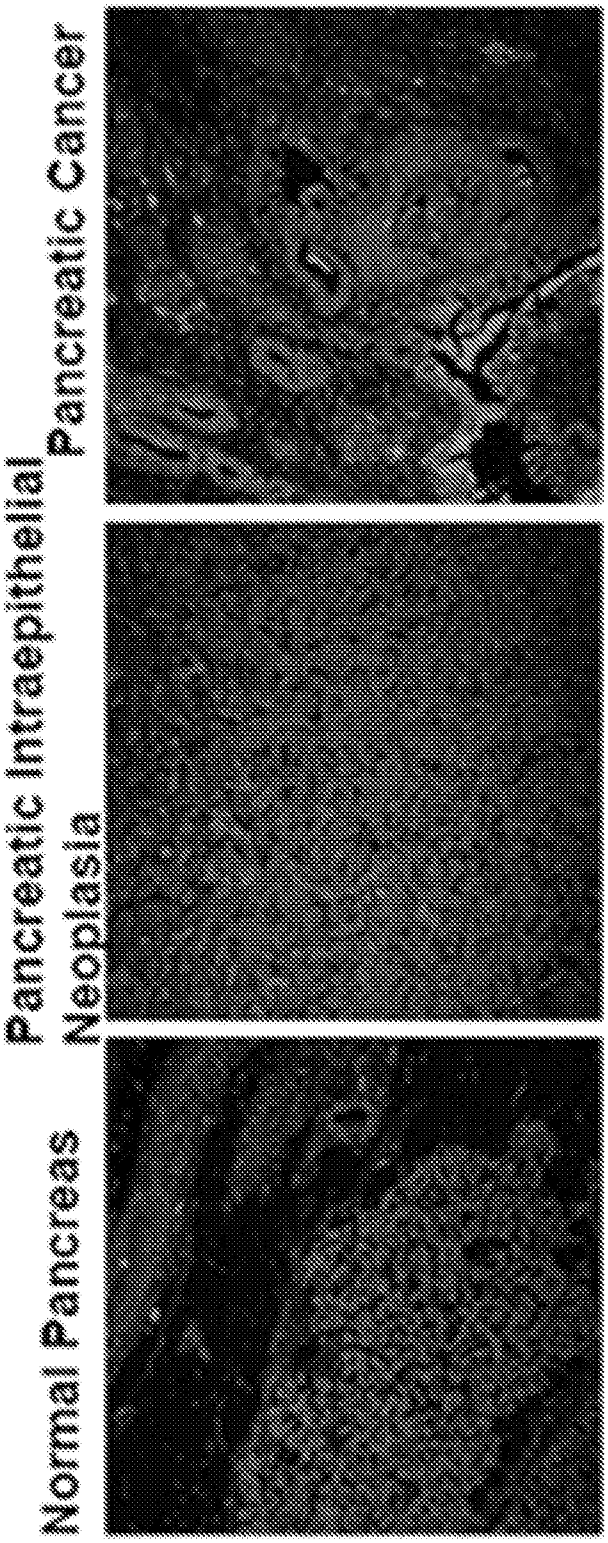
FIG. 9 illustrates fluorescence images showing binding patterns of ZD2-Cy5.5 to EDB-FN in specimens of human pancreatic cancer, pancreatic intraepithelial neoplasia and normal pancreas.

The expression of EDB-FN was first demonstrated in 4 different human pancreatic cancer cell lines, including BXPC3, Capan-1, Panc 10.05 and Panc-1 cells, with western blotting. These human PaCa cell lines are commonly used to develop mouse PaCa cancer models in preclinical studies. All of the tested cancer cell lines have high expression of EDB-FN, FIG. 9A. Tumor models were developed by subcutaneous implantation of the cancer cells in the flanks of female nude mice according to the instructions from ATCC. EDB-FN expression is demonstrated in the tumor xenografts of the human PaCa cells using immunofluorescence staining with BC-1 anti-EDB-FN monoclonal antibody. As shown in FIG. 9B, substantial expression of EDB-FN was observed in all four PaCa subtypes, and no expression was observed in normal pancreas and muscle, consistent with the reported results. High expression of EDB-FN was observed in the ECM of the PaCa tumors. The results indicate that EDB-FN is highly expressed by PaCa cells and tumors and is a promising oncoprotein target for molecular imaging and detection of PaCa.

ZD2 Peptide Binding to EDB-FN in PaCa Tumors

Figure 10:
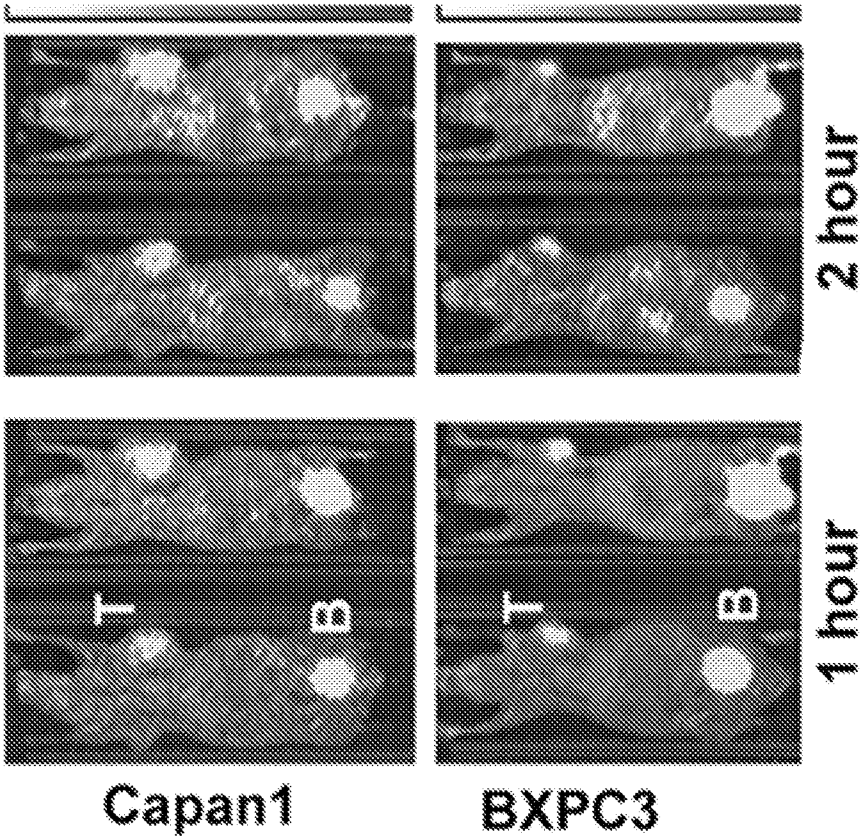
FIG. 10 illustrates two-dimensional coronal PET/CT images of mice bearing Capan-1 and BXPC3 human pancreatic cancer xenografts at 1 and 2 hr after intravenous injection of ZD2-($^{68}$Ga-NOTA) at a dose of 300 μCi/mouse. T: tumor; B: bladder.

A ZD2 peptide (Thr-Val-Arg-The-Ser-Ala-Asp) targeted fluorescence tracer ZD2-Cy5.5 was synthesized according to a reported method to assess the binding of the peptide to EDB-FN in PaCa tumors. The binding specificity of ZD2 peptide to EDB-FN in pancreatic cancer has been tested by incubation of ZD2-Cy5.5 with tumor slides of the above tumor xenografts. As shown in FIG. 10, strong binding of ZD2-Cy5.5 (red) was observed in all 4 tested tumor tissues, similar to the immunofluorescence staining in FIG. 9B. No significant binding of ZD2-Cy5.5 was observed to the normal pancreas and muscle. The strong binding of ZD2-Cy5.5 to EDB-FN in PaCa was blocked by BC-1 anti-EDB-FN monoclonal antibody (BC-1/ZD2). Little red fluorescence staining was observed for the PaCa specimens pre-incubated with BC-1 antibody and followed by ZD2-Cy5.5 (BC-1/ZD2). The results suggest that both ZD2-Cy5.5 and BC-1 specifically bind to the same EDB-FN protein target in the tumor tissues. ZD2 peptide is a promising targeting agent for specific binding of EDB-FN in PaCa tumors.

Expression of EDB-FN in Human PaCa Tumors

Figure 11:
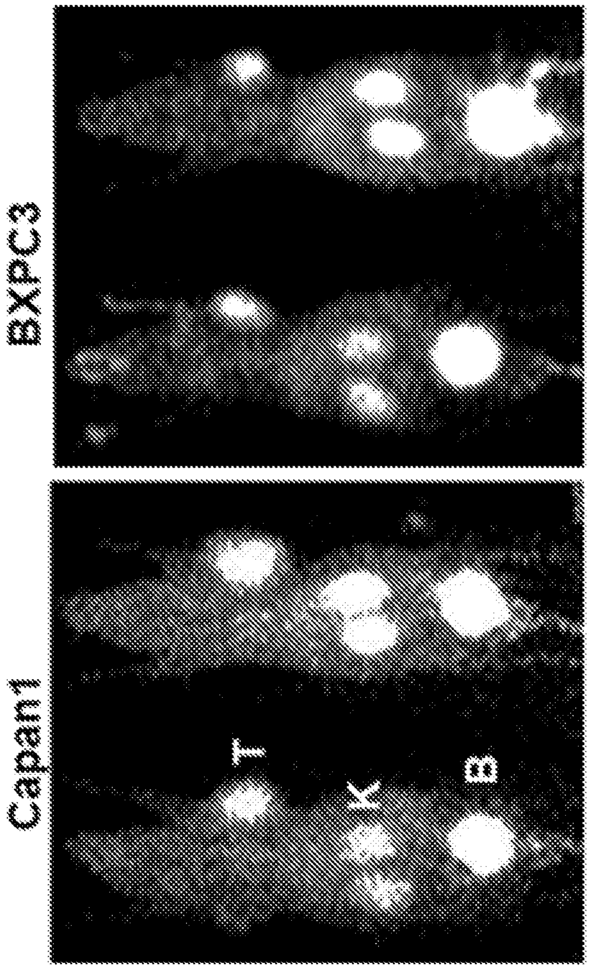
FIG. 11 illustrates three-dimensional PET images of mice bearing Capan-1 and BXPC3 human PaCa xenografts at 1 hr after intravenous injection of ZD2-($^{68}$Ga-NOTA) at a dose of 300 μCi/mouse. T: tumor; K: kidneys; B: bladder.

EDB-FN expression in human pancreatic cancer is demonstrated by staining human pancreatic cancer specimens with ZD2-Cy5.5. As shown in FIG. 11, strong red fluorescence was observed in a human PaCa specimen, little fluorescence in a normal pancreas, while some fluorescence intensity was seen in precancerous pancreatic intraepithelial neoplasia. The fluorescence intensity suggests high EDB-FN expression in PaCa, low expression in precancerous tissues, and no expression in normal pancreas.

PET Imaging of PaCa with ZD2-($^{68}$Ga-NOTA)

Figure 12:
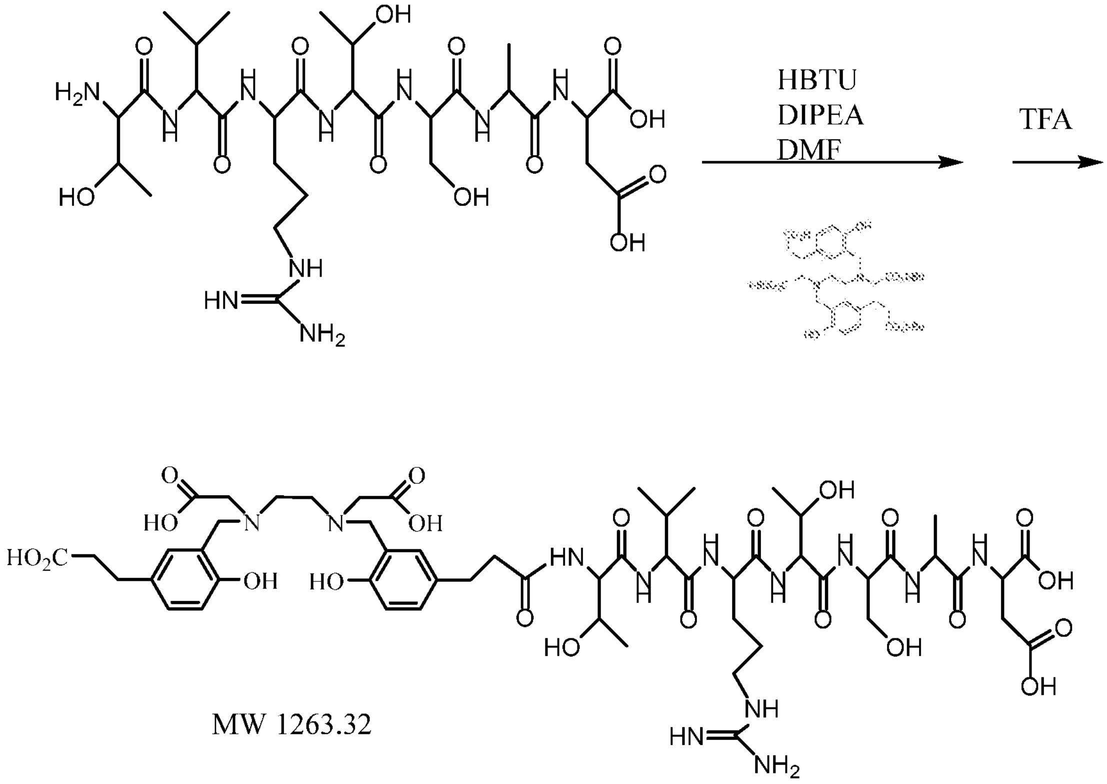
FIG. 12 illustrates a schematic showing the synthesis of ZD2-HBED-CC.
Figure 13:
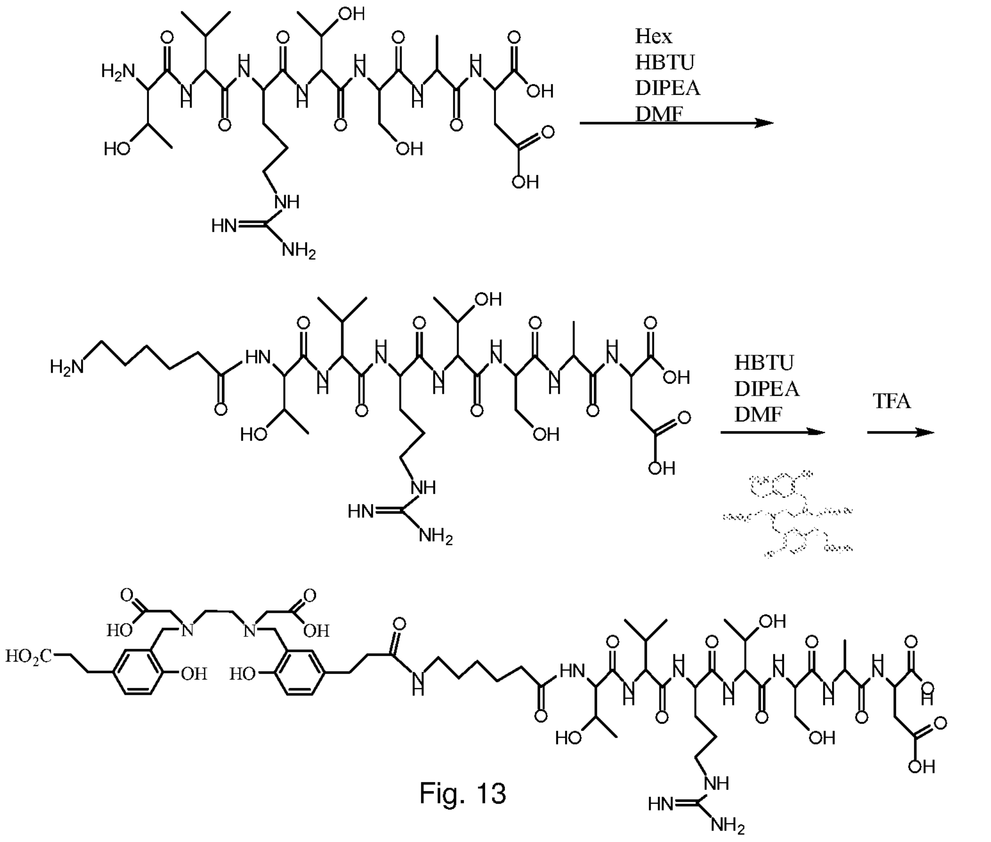
FIG. 13 illustrates a schematic showing the synthesis of ZD2-AH-HBED-CC.
Figure 14:
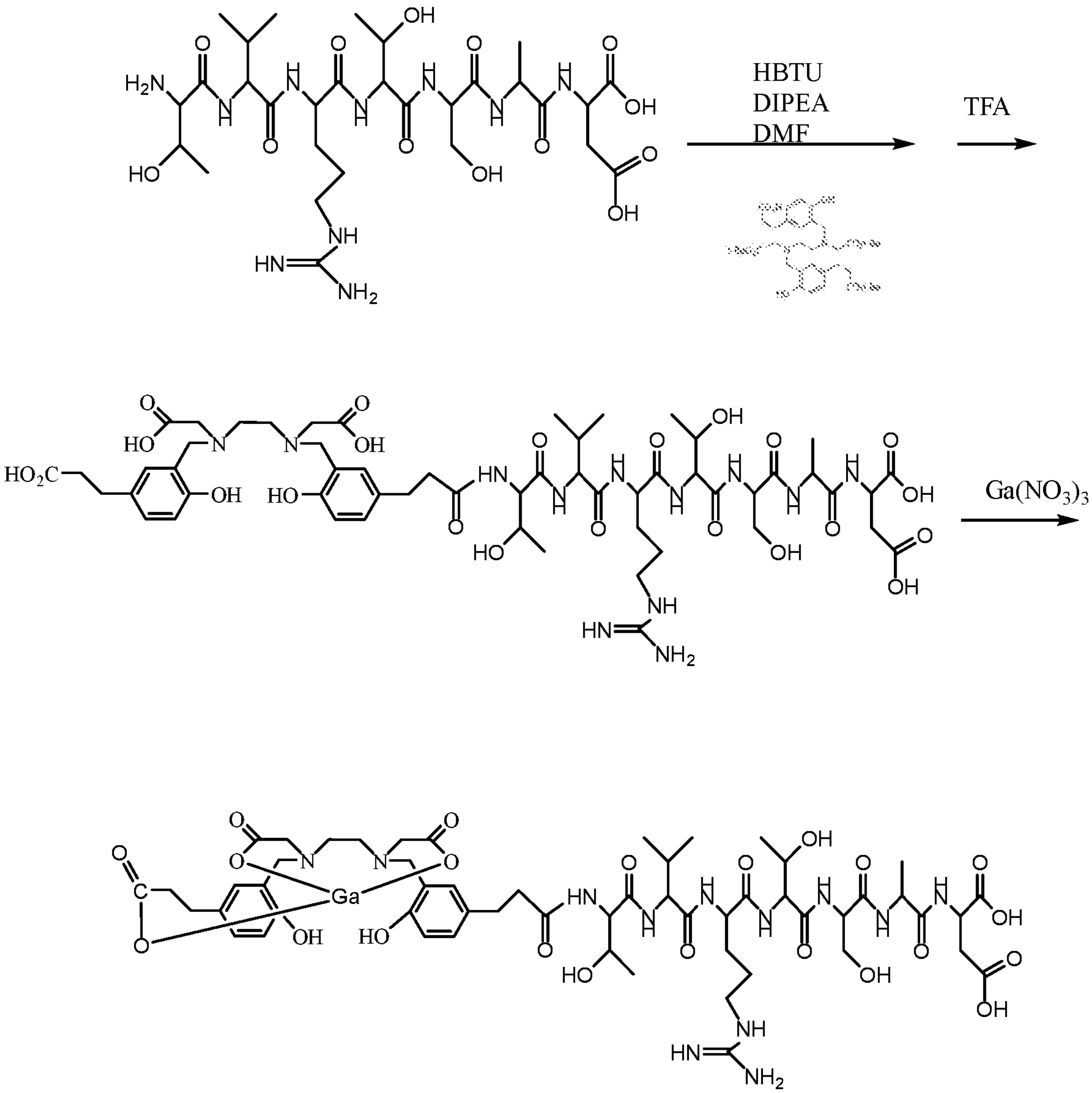
FIG. 14 illustrates a schematic showing the synthesis of ZD2-(Ga-HBED-CC).
Figure 15:
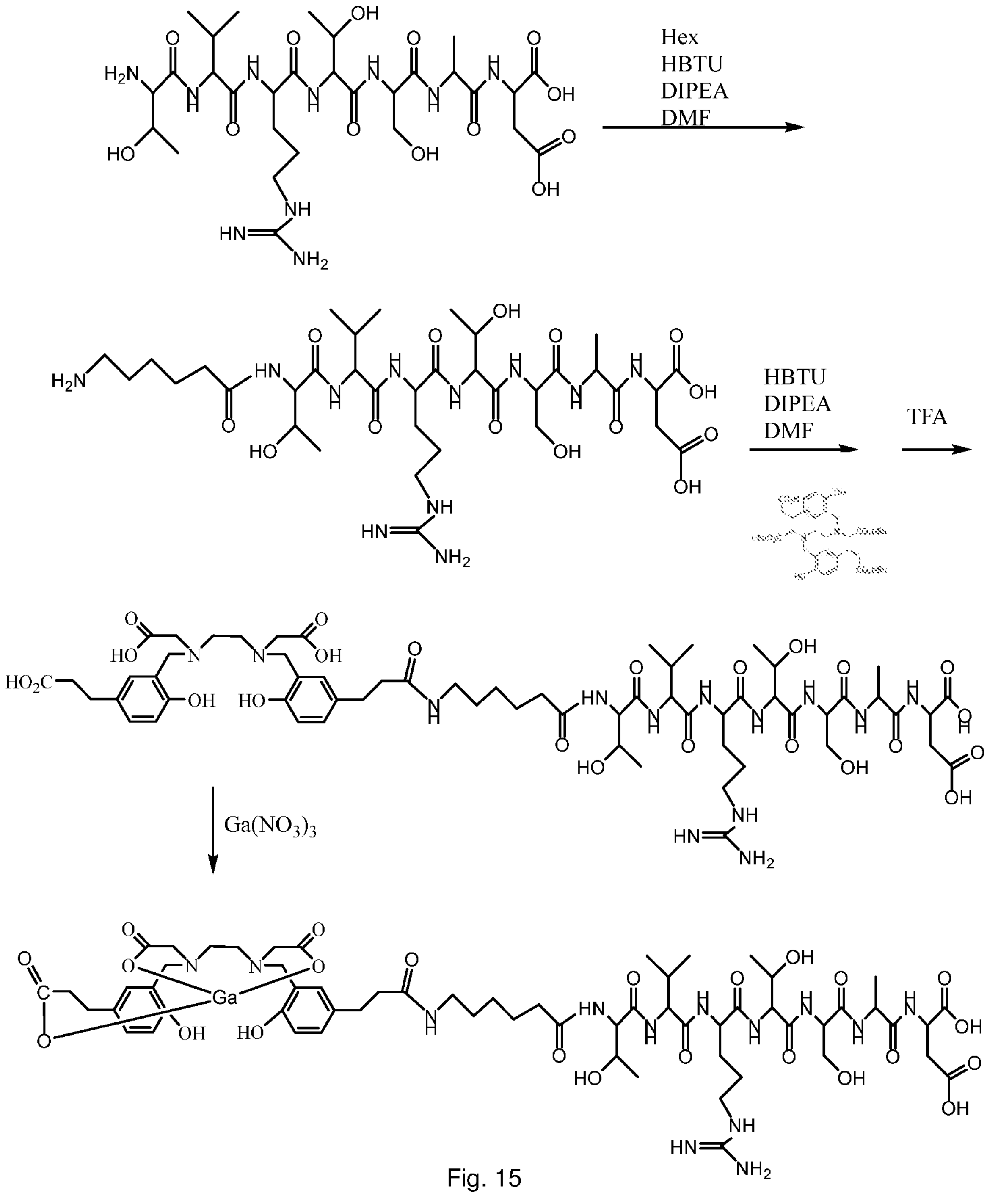
FIG. 15 illustrates a schematic showing the synthesis of ZD2-AH-(Ga-HBED-CC).
Figure 16:
FIG. 16 illustrates PET/CT images of mice bearing BXPC3 and Capan-1 human pancreatic tumor xenografts with ZD2-($^{68}$Ga-HBED-CC).
Figure 17:
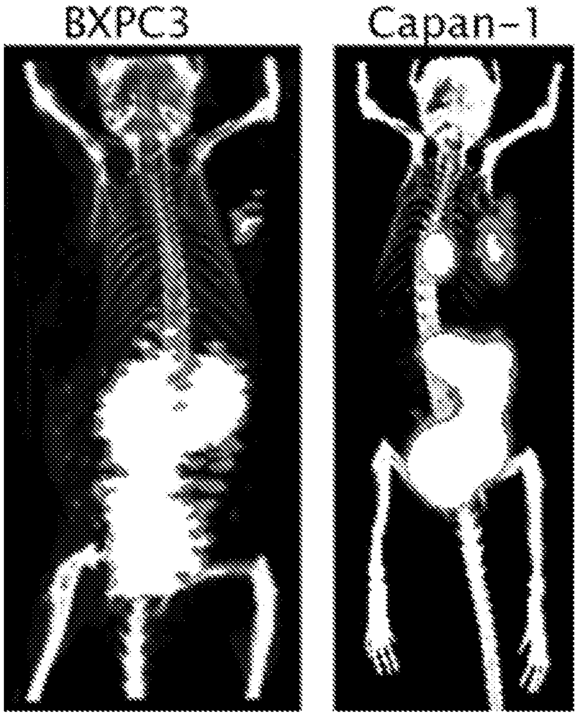
FIG. 17 illustrates PET/CT images of mice bearing BXPC3 and Capan-1 human pancreatic tumor xenografts with ZD2-AH-($^{68}$Ga-HBED-CC).

The effectiveness of ZD2-($^{68}$Ga-NOTA) for sensitive molecular imaging of EDB-FN and detection of PaCa was assessed in mouse models bearing Capani and BXPC3 human PaCa xenografts on a microPET/CT. The tumor models were similarly developed in female nude mice as in C.1. The tracer synthesized using the method above was intravenously injected at a dose of 300 μCi per mouse. FIG. 12 shows the representative 2D coronal PET/CT images showing the tumors at 1 and 2 hours postinjection of the tracer. Strong uptake of the tracer was observed in the tumors and the bladder at both time points. Little uptake was observed in the normal tissues and organs, especially in the brain, liver and lung, at 1 hr post-injection. Background noise was slightly increased at 2 hr post-injection possibly due to decreased radioactivity and longer scanning time. The signal intensity in both tumors was approximately 5 fold of that in the muscle at 1 and 2 hr post-injection. Three-dimensional PET images also revealed strong uptake in the tumors with little non-specific uptake in the surrounding normal tissues and organs other than the kidneys and bladder, FIG. 13. High signal intensity in the kidneys and bladder indicates that the tracer is mainly excreted via renal filtration. These results demonstrate the effectiveness and high specificity of ZD2-($^{68}$Ga-NOTA) for molecular imaging of EDB-FN and early detection of PaCa and further validate the specific expression of EDB-FN in PaCa. ZD2 peptide targeted $^{68}$Ga chelates are promising for sensitive early detection of pancreatic cancer in clinical practice.

Example 3

Synthesis of ZD2-HBED-CC

ZD2 peptide was synthesized using standard solid-phase chemistry. Then HBED-CC-tris(tBu) ester was conjugated to N-terminus of ZD2 peptide on the resin. After that, the peptide was cleaved from the resin using a cocktail of TFA/water/TIBS (96.5/2.5/1). The product was precipitated in ethyl ether, purified by preparative HPLC, lyophilized, and characterized by MALDI-TOF mass spectrometry. (M+1) m/z, 1264.02 observed; 1264.32 calculated for $C_{55}H_{82}N_{12}O_{22}$.

Synthesis of ZD2-AH-HBED-CC

ZD2 peptide was synthesized using standard solid-phase chemistry. Then Fmoc-6-aminohexanoic acid was conjugated to N-terminus of ZD2 peptide on the resin. After that, HBED-CC-tris(tBu) ester was reacted with the peptide, which was followed by the cleavage from the resin using a cocktail of TFA/water/TIBS (96.5/2.5/1). The product ZD2-AH-HBED-CC was precipitated in ethyl ether, purified by preparative HPLC, lyophilized, and characterized by MALDI-TOF mass spectrometry. (M+1) m/z, 1377.1 observed; 1377.48 calculated for $C_{61}H_{93}N_{13}O_{23}$.

Synthesis of ZD2-(Ga-HBED-CC)

The ligand, ZD2-HBED-CC without a linker, and gallium nitrate were mixed in PBS at 90° C. for 2 min. Then the product ZD2-(Ga-HBED-CC) was purified by preparative HPLC and characterized by MALDI-TOF mass spectrometry. (M+1) m/z, 1329.8 observed; 1329.47 calculated for $C_{55}H_{79}GaN_{12}O_{22}$.

Synthesis of ZD2-AH-(Ga-HBED-CC)

The ligand, ZD2-HBED-CC with a linker, and gallium nitrate were mixed in PBS at 90° C. for 2 min. Then the product ZD2-AH-(Ga-HBED-CC) was purified by preparative HPLC and characterized by MALDI-TOF mass spectrometry. (M+1) m/z, 1442.9 observed; 1442.55 calculated for $C_{61}H_{90}GaN_{13}O_{23}$.

PET Imaging of Mice with Tumors

All in vivo imaging studies were conducted in accordance with CWRU Animal Research Committee-approved protocols and guidelines. Mice bearing BxPC3 or Capan-1 human pancreatic xenografts were anesthetized with 2% isoflurane in oxygen. Tracer ZD2-($^{68}$Ga-HBED-CC) or ZD2-AH-($^{68}$Ga-HBED-CC) was injected at a dose of 100-300 μCi [5.3-13.0 MBq] via a tail vein. Then mice underwent 10-min or 20-min static PET scans (Inveon microPET, Siemens Medical Solutions USA Inc.) after 30 min or 60 min uptake period. All PET procedures were followed with CT scans for anatomical co-registration. PET/CT images were analyzed using Inveon Research Workplace version 3.0 and Horos software. Regions of interest (ROIs) were drawn for the tumors, major organs and muscle, to calculate the ratio of specific and non-specific tissue uptake. Images were processed with 3D reconstruction with a zoom factor of 1.0 using 3D-OSEM with two iterations followed by MAP with 18 iterations.

The effectiveness of ZD2-($^{68}$Ga-HBED-CC) for sensitive molecular imaging of EDB-FN and detection of pancreatic cancer was assessed in the mouse models bearing Capan-1 and BxPC3 human pancreatic cancer xenografts on a micro-PET/CT. Figures demonstrate the representative 2D as well as 3D whole body PET/CT images of the tumor bearing mice at 30 min or 60 min post-injection. Strong uptake of the tracer was observed in the tumors, kidneys and bladder at 30 min or 60 min post-injection as shown in the whole-body PET images. The uptake of the tracers in both tumors were substantially higher than the normal organs and tissues, including the brain, heart, liver, and muscle. High signal intensity in the kidneys and bladder indicates that the tracer is mainly excreted via renal filtration.

Quantitative analysis revealed that the uptake in both BxPC3 and Capan-1 tumors was significantly higher than the normal tissues, including brain, heart, liver and muscle, at 30 min or 60 min post-injection. For ZD2-AH-($^{68}$Ga-HBED-CC), the tumor uptake was approximately 18.3 and 13 fold of that of the muscle ($p<0.01$) for BxPC3 and Capan-1 tumors, respectively at 60 min post-injection. For ZD2-($^{68}$Ga-HBED-CC) without a linker, the tumor uptake was approximately 10.2 and 7.3 fold of that of the muscle ($p<0.01$) for BxPC3 and Capan-1 tumors, respectively at 60 min post-injection. The tumor uptake remained significantly higher than the normal tissues in both tumor models ($p<0.05$). These results demonstrate that both ZD2-($^{68}$Ga-HBED-CC) and ZD2-AH-($^{68}$Ga-HBED-CC) are highly specific to pancreatic cancer tumors with minimal uptake in normal tissues, including the liver.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A PET/SPECT probe comprising formula:

P-L-C wherein P is a peptide that binds to extradomain-B fibronectin (EDB-FN) or extradomain-A fibronectin (EDA-FN) and that includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 19, SEQ ID NO: 20, SEQ ID NO: 21, SEQ ID NO: 22, SEQ ID NO: 23, SEQ ID NO: 24, and retro-inverso amino acid sequences thereof; C is a PET/SPECT contrast agent; and L is an optional linker that covalently links the peptide to the PET/SPECT contrast agent, wherein the contrast agent is a metal chelating agent comprising at least one of diethylenetriaminepentaacetate (DTPA), 1,4,7,10-tetraazadodecanetetraacetate (DOTA), 1,4,7,10-tetraazadodecane-1,4,7-triacetate (DO3A), ethylenediaminetetraacetate (EDTA), 1,4,7,10-tetraazacyclotridecanetetraacetic acid (TRITA), 1,4,8,11-tetraazacyclotetradecane-1,4,8,11-tetraacetic acid (TETA), 1,4,7,10-tetraazadodecanetetramethylacetate (DOTMA), 1,4,7,10-tetraazadodecane-1,4,7-trimethylacetate (DO3MA), N,N',N'',N'''-tetraphosphonatomethyl-1,4,7,10-tetraazacyclododecane (DOTP), 1,4,7,10-tetraazacyclododecane-1,4,7,10-tetrakis(methylene methylphosphonic acid) (DOTMP), 1,4,7,10-tetraazacyclododecane-1,4,7,10-tetrakis(methylene phenylphosphonic acid) (DOTPP), N,N'-ethylenedi-L-cysteine, and salts or esters thereof.

2. The probe of claim 1, wherein the linker is an aliphatic, heteroaliphatic, cyclic, or heterocyclic linker.

3. The probe of claim 1, wherein the linker is an alkylene, alkylene oxide, arylene, or alkylenearylene linker that covalently links the peptide and contrast agent.

4. The probe of claim 1, having the formula:

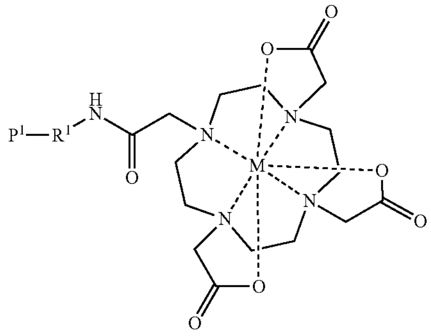

wherein:

$P_1$ is a peptide having an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 19, SEQ ID NO: 20, SEQ ID NO: 21, SEQ ID NO: 22, SEQ ID NO: 23, and SEQ ID NO: 24;

$R^1$ is an optional linker and if present is an alkylene, alkylene oxide, arylene, or alkylenearylene linker; and M is a metal selected from the group consisting of $^{67}$Ga, $^{68}$Ga, $^{64}$Cu, $^{99m}$Tc, $^{111}$In, $^{89}$Zr, $^{90}$Y, $^{153}$Sm, or $^{89}$Sr; or salts thereof.

5. A method of detecting cancer cells in tissue of a subject comprising:

contacting the tissue of the subject with a PET/SPECT probe, the PET/SPECT probe comprising the following formula:

P-L-C wherein P is a peptide that binds to extradomain-B fibronectin (EDB-FN) or extradomain-A fibronectin (EDA-FN) and that includes an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 19, SEQ ID NO: 20, SEQ ID NO: 21, SEQ ID NO: 22, SEQ ID NO: 23, SEQ ID NO: 24, and retro-inverso amino acid sequences thereof; C is a PET/SPECT contrast agent; and L is an optional linker that covalently links the peptide to the PET/SPECT contrast agent, wherein the contrast agent is a metal chelating agent comprising at least one of diethylenetriaminepentaacetate (DTPA), 1,4,7,10-tetraazadodecanetetraacetate (DOTA), 1,4,7,10-tetraazadodecane-1,4,7-triacetate (DO3A), ethylenediaminetetraacetate (EDTA), 1,4,7,10-tetraazacyclotridecanetetraacetic acid (TRITA), 1,4,8,11-tetraazacyclotetradecane-1,4,8,11-tetraacetic acid (TETA), 1,4,7,10-tetraazadodecanetetramethylacetate (DOTMA), 1,4,7,10-tetraazadodecane-1,4,7-trimethylacetate (DO3MA), N,N',N'',N'''-tetraphosphonatomethyl-1,4,7,10-tetraazacyclododecane (DOTP), 1,4,7,10-tetraazacyclododecane-1,4,7,10-tetrakis(methylene methylphosphonic acid) (DOTMP), 1,4,7,10-tetraazacyclododecane-1,4,7,10-tetrakis(methylene phenylphosphonic acid) (DOTPP), N,N'-ethylenedi-L-cysteine, and salts or esters thereof; and detecting a location and/or distribution of cancer cells in the tissue by detecting the PET/SPECT probe in the tissue of the subject.

6. The method of claim 5, wherein the contacting step is in vivo.

7. The method of claim 5, wherein the PET/SPECT probe is systemically administered to the subject having or suspected of having cancer.

8. The method of claim 7, wherein the cancer comprises at least one of breast cancer, liver cancer, stomach cancer, colon cancer, pancreatic cancer, ovarian cancer, lung cancer, kidney cancer, prostate cancer, testicular cancer, glioblastoma, sarcoma, bone cancer, brain cancer, head and neck cancers, or skin cancer.

9. The method of claim 5, wherein the subject has cancer and the PET/SPECT probe is administered to the tissue of the subject to determine cancer aggressiveness.

10. The method of claim 5, wherein the linker is an aliphatic, heteroaliphatic, cyclic, and/or heterocyclic linker.

11. The method of claim 5, wherein the linker includes an alkylene, alkylene oxide, arylene, or alkylenearylene linker that covalently links the peptide and contrast agent.

12. The method of claim 5, the PET/SPECT probe having the formula:

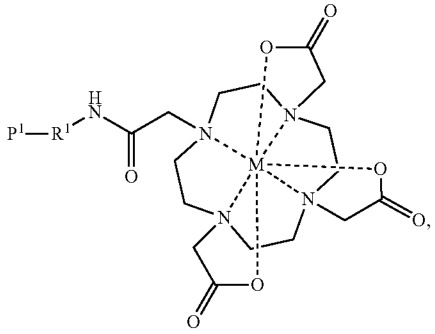

wherein:

$P_1$ is a peptide having an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 19, SEQ ID NO: 20, SEQ ID NO: 21, SEQ ID NO: 22, SEQ ID NO: 23, SEQ ID NO: 24, and retro-inverso amino acid sequences thereof;

$R^1$ is optional linker and if present is an alkylene, alkylene oxide, arylene, or alkylenearylene linker; and M is a metal selected from the group consisting of $^{67}Ga$, $^{68}Ga$, $^{64}Cu$, $^{99m}Tc$, $^{111}In$, $^{89}Zr$, $^{90}Y$, $^{153}Sm$, or $^{89}Sr$; or salts thereof.

13. The method of claim 5, wherein the cancer is prostate cancer.

* * * * *

SEQUENCE LISTING

```
<160> NUMBER OF SEQ ID NOS: 30

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

Thr Val Arg Thr Ser Ala Asp
1               5


<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Asn Trp Gly Asp Arg Ile Leu
1               5


<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Asn Trp Gly Lys Pro Ile Lys
1               5


<210> SEQ ID NO 4
<211> LENGTH: 7
<212> TYPE: PRT
<213> ORGANISM: Artificial Sequence
<220> FEATURE:
<223> OTHER INFORMATION: Synthetic Construct

<400> SEQUENCE: 4

Ser Gly Val Lys Ser Ala Phe
1               5


<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Gly Val Lys Ser Tyr Asn Glu
1               5


<210> SEQ ID NO 6
<211> LENGTH: 7
<212> TYPE: PRT
<213> ORGANISM: Artificial Sequence
```

-continued

<220> FEATURE:
<223> OTHER INFORMATION: Synthetic Construct

<400> SEQUENCE: 6

Ile Gly Lys Thr Asn Thr Leu
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Ile Gly Asn Ser Asn Thr Leu
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

Ile Gly Asn Thr Ile Pro Val
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Leu Tyr Ala Asn Ser Pro Phe
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Cys Thr Val Arg Thr Ser Ala Asp Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Cys Asn Trp Gly Asp Arg Ile Leu Cys
1               5

<210> SEQ ID NO 12
<211> LENGTH: 9
<212> TYPE: PRT
<213> ORGANISM: Artificial Sequence
<220> FEATURE:

-continued

<223> OTHER INFORMATION: Synthetic Construct

<400> SEQUENCE: 12

Cys Asn Trp Gly Lys Pro Ile Lys Cys
1 5

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Cys Ser Gly Val Lys Ser Ala Phe Cys
1 5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct

<400> SEQUENCE: 14

Cys Gly Val Lys Ser Tyr Asn Glu Cys
1 5

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Cys Ile Gly Lys Thr Asn Thr Leu Cys
1 5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Cys Ile Gly Asn Ser Asn Thr Leu Cys
1 5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Cys Ile Gly Asn Thr Ile Pro Val Cys
1 5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Cys Leu Tyr Ala Asn Ser Pro Phe Cys
1 5

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Trp Asn Tyr Pro Phe Arg Leu
1 5

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

Ser Asn Thr Ser Tyr Val Asn
1 5

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Ser Phe Ser Tyr Thr Ser Gly
1 5

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Trp Ser Pro Ala Pro Met Ser
1 5

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Thr Arg Glu His Pro Ala Gln
1 5

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Ala Arg Ile Ile Asp Asn Ala
1 5

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Cys Trp Asn Tyr Pro Phe Arg Leu Cys
1 5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Cys Ser Asn Thr Ser Tyr Val Asn Cys
1 5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Cys Ser Phe Ser Tyr Thr Ser Gly Cys
1 5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Cys Trp Ser Pro Ala Pro Met Ser Cys
1 5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Cys Thr Arg Glu His Pro Ala Gln Cys
1 5

-continued

```
<210> SEQ ID NO 30
<211> LENGTH: 9
<212> TYPE: PRT
<213> ORGANISM: Artificial Sequence
<220> FEATURE:
<223> OTHER INFORMATION: Synthetic Construct

<400> SEQUENCE: 30

Cys Ala Arg Ile Ile Asp Asn Ala Cys
1               5
```